(12) United States Patent
Kruger et al.

(10) Patent No.: US 11,701,092 B2
(45) Date of Patent: Jul. 18, 2023

(54) AUTOMATED ULTRASOUND APPARATUS AND METHODS TO NON-INVASIVELY MONITOR FLUID RESPONSIVENESS

(71) Applicant: THE REGENTS OF THE UNIVERSITY OF MICHIGAN, Ann Arbor, MI (US)

(72) Inventors: Grant Kruger, Ann Arbor, MI (US); Torben K. Becker, Gainesville, FL (US); Nikhil Theyyunni, Ann Arbor, MI (US); Ross Kessler, Ann Arbor, MI (US); Bradley Plummer, Ann Arbor, MI (US); Matthew Tafoya, Oakland, CA (US); Chelsea Tafoya, Oakland, CA (US); Steven E. Harte, Livonia, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 274 days.

(21) Appl. No.: 16/611,470

(22) PCT Filed: May 10, 2018

(86) PCT No.: PCT/US2018/032152
§ 371 (c)(1),
(2) Date: Nov. 6, 2019

(87) PCT Pub. No.: WO2018/209140
PCT Pub. Date: Nov. 15, 2018

(65) Prior Publication Data
US 2020/0163650 A1 May 28, 2020

Related U.S. Application Data

(60) Provisional application No. 62/504,199, filed on May 10, 2017.

(51) Int. Cl.
*A61B 8/08* (2006.01)
*A61B 8/02* (2006.01)
(Continued)

(52) U.S. Cl.
CPC .............. *A61B 8/5207* (2013.01); *A61B 8/02* (2013.01); *A61B 8/06* (2013.01); *A61B 8/4236* (2013.01);
(Continued)

(58) Field of Classification Search
CPC .......... A61B 8/5207; A61B 8/02; A61B 8/06; A61B 8/4236; A61B 8/4254; A61B 8/5223; A61B 8/5276
See application file for complete search history.

(56) References Cited

U.S. PATENT DOCUMENTS

| 5,485,848 A | * | 1/1996 | Jackson | A61B 5/0002 |
| | | | | 600/485 |
| 6,019,726 A | * | 2/2000 | Webb | A61B 8/12 |
| | | | | 600/459 |

(Continued)

FOREIGN PATENT DOCUMENTS

| JP | 5998197 B2 * | 9/2016 | ........... A61B 8/4218 |
| WO | WO-2013/124946 A1 | 8/2013 | |

OTHER PUBLICATIONS

JP-5998197-B2. Translated by Espacenet. Sep. 28, 2016 (retrieved on Nov. 4, 2021) (Year: 2021).*

(Continued)

*Primary Examiner* — Keith M Raymond
*Assistant Examiner* — Andrew W Begeman
(74) *Attorney, Agent, or Firm* — Marshall, Gerstein & Borun LLP

(57) ABSTRACT

A fully automated ultrasound apparatus includes a sensor or probe which can be initially manually attached to a side of
(Continued)

the neck of a patient, an ultrasound interface to control the sensor and periodically acquire raw ultrasound data, a signal and image processing system to autonomously convert the raw ultrasound data into a measurement that is useful to physicians, and a display to relay the current measurements and measurement history to provide data trends. The sensor can include one or more ultrasound transducers built into a housing. A disposable component can serve to secure the sensor to the neck of the patient and to provide a coupling medium between the sensor and the skin of the patient.

27 Claims, 14 Drawing Sheets

(51) Int. Cl.
*A61B 8/06* (2006.01)
*A61B 8/00* (2006.01)

(52) U.S. Cl.
CPC .......... *A61B 8/4254* (2013.01); *A61B 8/5223* (2013.01); *A61B 8/5276* (2013.01)

(56) References Cited

U.S. PATENT DOCUMENTS

| | | | |
|---|---|---|---|
| 9,572,519 B2* | 2/2017 | Shmarak | A61B 5/7207 |
| 2002/0120193 A1* | 8/2002 | Chiang | G01S 15/892 |
| | | | 128/920 |
| 2004/0073105 A1 | 4/2004 | Hamilton et al. | |
| 2006/0211942 A1 | 9/2006 | Hoctor et al. | |
| 2006/0235301 A1* | 10/2006 | Chalana | A61B 8/565 |
| | | | 600/443 |
| 2007/0167809 A1 | 7/2007 | Dala-Krishna | |
| 2011/0075888 A1* | 3/2011 | Matsumoto | G06T 5/50 |
| | | | 345/589 |
| 2012/0065479 A1 | 3/2012 | Lahiji et al. | |
| 2012/0283564 A1* | 11/2012 | Ebbini | A61B 8/06 |
| | | | 600/443 |
| 2013/0303915 A1* | 11/2013 | Barnard | A61B 8/461 |
| | | | 600/449 |
| 2014/0064582 A1 | 3/2014 | Schmidt et al. | |
| 2014/0323824 A1 | 10/2014 | Addison et al. | |
| 2014/0363065 A1* | 12/2014 | Taerum | G16H 40/63 |
| | | | 382/131 |
| 2016/0345930 A1* | 12/2016 | Mizukami | A61B 8/02 |
| 2018/0353157 A1* | 12/2018 | Eibl | A61B 8/06 |
| 2021/0106305 A1* | 4/2021 | Wang | A61B 8/483 |

OTHER PUBLICATIONS

Kent et al., "Sonographic evaluation of intravascular volume status: Can internal jugular or femoral vein collapsibility be used in the absence of IVC visualization?", 2015, Annals of Thoracic Medicine, vol. 10 Issue 1 (Year: 2015).*
Garijo et al., "Correlation Between Transhepatic and Subcostal Inferior Vena Cava Views to Assess Inferior Vena Cava Variation: A Pilot Study", Mar. 30, 2017, Journal of Cardiothoracic and Vascular Anesthesia, 31, 973-979 (Year: 2017).*
Fenster et al., "Three-Dimensional Ultrasound Scanning", 2011, Interface Focus, 1, 503-519 (Year: 2011).*
Kalashyan et al., "Single sweep three-dimensional carotid ultrasound: Reproducibility in plaque and artery volume measurements", 2014, Atherosclerosis 232, 397-402 (Year: 2014).*
Marks et al., "Interactive 3D Analysis of Blood Vessel Trees and Collateral Vessel volumes in Magnetic Resonance Angiograms in the Mouse Ischemic Hindlimb Model", Feb. 20, 2014, Open Med Imagining J. 7, p. 19-27 (Year: 2014).*
International Preliminary Report on Patentability from International Application No. PCT/US2018/032152 dated Nov. 12, 2019.
International Search Report and Written Opinion from International Application No. PCT/US18/32152 dated Oct. 12, 2018.
Miller et al., "Predicting and measuring fluid responsiveness with echocardiography," In: Echo Res Pract., 45 pages (2016).

* cited by examiner

AUTOMATED ULTRASOUND APPARATUS AND METHODS TO NON-INVASIVELY MONITOR FLUID RESPONSIVENESS

CROSS-REFERENCE TO RELATED APPLICATION

This application is a U.S. National Phase of International Application No. PCT/US2018/032152, filed May 10, 2018, which claims the priority benefit under 35 U.S.C. § 119(e) of U.S. Provisional Application No. 62/504,199, filed May 10, 2017, entitled "Automated Ultrasound Apparatus and Methods to Non-Invasively Monitor Fluid Responsiveness," the disclosure of which is incorporated herein by reference in its entirety.

STATEMENT REGARDING FEDERALLY SPONSORED RESEARCH OR DEVELOPMENT

This invention was made with government support under 1600236 awarded by the National Science Foundation Innovation Corps. The government has certain rights in the invention.

FIELD OF THE DISCLOSURE

The present disclosure relates generally to medical devices and, more particularly, to techniques for utilizing ultrasound imaging to autonomously monitor changes in a vessel, such as geometric changes.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Fluid resuscitation is a commonly performed procedure to ensure adequate perfusion of the internal organs of a patient that suffers from a variety of conditions. For example, organs can experience shock, sepsis, hemorrhage and/or gastrointestinal disorders under a number of unique circumstances. While it may be essential to undertake early aggressive fluid therapy on the organ or organs, excess fluids can be harmful when the circulatory system becomes "overloaded" and is no longer fluid-responsive.

Excess fluid can result in tissue or pulmonary edema, respiratory insufficiency, renal failure, and/or congestive heart failure, among other potentially dangerous problems. Conversely, potentially dangerous outcomes may occur if an inadequate or insufficient amount of fluid is provided to the tissue. For example, inadequate fluid supply can place a patient at risk for circulatory disturbances, shock, and/or pre-renal failure.

The lack of an accurate and reliable objective fluid-responsiveness measurement technique has limited adoption of goal-directed fluid therapy strategies. Recent studies have shown that early identification of fluid overload can reduce mortality, recovery time, and the amount of time spent on artificial ventilation. Accordingly, it is critical to know when to end fluid resuscitation and to modify treatment strategies to maintain cardiac output, thereby ensuring adequate tissue perfusion.

Presently, physicians and medical facilities lack objective tools for quantifying fluid management in a way that improves patient outcomes. Currently, professionals perform cardiac output measurements as an alternative for fluid responsiveness assessments. Cardiac output can be performed both invasively (e.g., by means of pulmonary artery catheterization) or non-invasively (e.g., through advanced echocardiography). However, due their invasiveness, technical challenges and/or operator-dependence, such methods are not routinely used. Additionally, it may not be possible to perform these measurements in many critically ill patients. Other invasive methods such a central venous pressure (CVP) are still commonly used. However, studies have shown that CVP is unreliable for guiding fluid therapy and can easily be confounded by other disease processes. This potential unreliability can be caused by blood pressure and flow measurements that rely on the assumption that vessel compliance is constant. Studies have revealed that certain conditions present in the patient may result in changes of vascular compliance, and thus result in poor accuracy when using the CVP method.

Ultrasound (US) technologies have been used to noninvasively assess fluid volume status by measuring the inferior vena cava (IVC) diameter. However, these approaches are also limited in effectiveness when used in conjunction with fluid management. Ultrasound technologies suffer from limited available clinical time, training hurdles, inadequate professional skills, and accessibility to the ultrasound systems. Additionally, ultrasound exams performed on critically ill patients may be limited by the inability of the patient to tolerate changes in body position and abnormal breathing, which are common occurrences in ill patients. Further still, patient habitus, bowel gas, or peritonitis can make an ultrasound exam of the upper abdomen, including the IVC, difficult even for experienced sonographers. While ultrasound devices are increasingly available in many critical care settings, using them to measure volume status requires specialized training and years of experience to build confidence. Even after obtaining a measurement, physicians must repeat this process periodically to monitor changes in volume status, which requires repeated access to ultrasound machines that are typically shared among numerous physicians. Accordingly, finding the machine can be a time-consuming undertaking that could be used to care for other patients.

Recent studies suggest that the ratio between the range and mean diameter of the internal jugular vein (IJ) over the respiratory cycle is predictive of volume responsiveness (VR) and that this measurement is well correlated to the similar IVC Collapsibility Index (CI) measurement. Bedside US systems are used to perform these measurements, but can be cumbersome, time-consuming, and subject to operator induced measurement variability. Using currently available clinical US systems to measure VR requires specialized training and experience to build competence over an extended period. In fact, some reports even suggest that manual US-based CI measurements may not accurately predict VR potentially due to operator-induced variability.

Ultrasound speckle tracking has previously been used to measure soft tissue and blood flow displacement versus time (velocity); typical algorithms to determine the displacement of a region of interest (ROI) utilize correlation-based approaches to match the ROI from an earlier image frame to a later frame. These algorithms are internal to the larger speckle tracking algorithm. Some other methods have also been developed to perform the function of ROI displacement measurement. Existing speckle tracking requires manual or semi-manual placement of the ROIs at specific points on the ultrasound image. In cases where ROI are evenly distributed across the entire image, a user would still need to select the data from a particular region for further investigation of the measurements. Clinically, speckle tracking has been used extensively for measuring tissue strain versus time in the heart during echocardiographic studies. It has also been used to provide improved image contrast when using ultrasound to evaluate potentially diseased soft tissues (i.e. breast lesions, tendons, etc.). All these measurements are performed utilizing strain, which requires the distance between two ROIs to be known.

SUMMARY OF THE INVENTION

To overcome the aforementioned problems associated with traditional ultrasound implementation, an ultrasound smart sensor system provided herein performs fully automated or semi-automated (i.e., nurse assisted) fluid status measurements similar to electrocardiograms, capnography, and/or pulse oximetry. A volume responsiveness (VR) sensor will fulfill a need for emergency and acute and critical care physicians by providing an automated, disposable, low-cost sensor that can be placed on the side of a patient's neck over the internal jugular vein (IJ) to obtain continuous and real-time assessments of a patient's fluid status.

In accordance with an embodiment, an example system can include a number of sub-systems: (i) a sensor or probe which can be attached to a side of the neck of a patient; (ii) an ultrasound interface to control the sensor and acquire raw ultrasound data; (iii) a signal and image processing system to convert the raw ultrasound data into a measurement that is useful to physicians; and (iv) a display to relay the current measurements and measurement history to provide data trends. The sensor can include one or more ultrasound transducers built into a housing. A disposable component can serve to secure the sensor to the neck of the patient and to provide a coupling medium between the sensor and the skin of the patient. In some examples, the display may be one of a stand-alone unit that is integrated with an existing bedside patient monitor system, or alternatively or additionally, the data may be sent directly to an electronic medical record of the patient for storage and display. Further, in some examples, the sensor may have a concave surface to enable the sensor to lay flush against a skin surface.

Ultrasound smart sensor systems provided herein can result in faster recovery, fewer complications and less complex interventions by avoiding fluid overload related injury of patients. In various examples, the systems do not require operator intervention once the systems have been correctly applied to a patient. The correct application of sensors may be achieved in a straightforward manner to identify anatomical landmarks on the skin surface to guide placement with no ultrasound specific training required. Further, the described sensors may be ultra-low profile and low-cost and may be provided in a wearable patch-type sensor to allow the sensor to be disposable, thus alleviating logistics related to medical facility equipment training. Generally, systems capable of steering 2-dimensional ultrasound scan planes such that it coincides with a target plane in the tissue require a large, costly 3-dimensional array probe. However, the presently-described systems are capable of doing so using only a low-profile wearable probe sensor. In particular, these sensors are used on 2-dimensional (2D) ultrasound data or other 2D image data.

Additionally, due to the small, lightweight configuration of the sensor, an operator need not physically hold the sensor against the patient in order to collect data. As previously stated, little to no user intervention is required as the sensor functions in a similar fashion to pulse oximetry and/or electrocardiograms.

In some examples, the transducer, or sensor head, embedded in the ultrasound smart sensor system can either be a 1-dimensional (1D) or 2-dimensional (2D) linear transducer, capacitive micromachined ultrasound transducer (CMUT), a mechanical wobbler, or similar system. In the case of the wobbler-type system, a novel method is employed that removes physical mechanical linkages between the actuator and a sensor head and utilizes magnetic fields to provide the linkages. Accordingly, the resulting system has fewer failure modes, wear effects, and seal failures and can be manufactured at a significantly reduced cost.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Provided are techniques for non-invasively, autonomously, and repeatedly measuring and recording changes of vessels over time using ultrasound technology. The ultrasound smart sensor system described herein performs fully automated or semi-automated (e.g., nurse-assisted) fluid status measurements similar to electrocardiograms, capnography, or pulse oximetry. An example sensor is a volume responsiveness (VR) sensor that can provide an automated, disposable, low-cost device that professionals can place on the side of a patient's neck, over the internal jugular vein (IA to obtain continuous and real-time assessments of a patient's fluid status. Generally speaking, the VR sensor is first applied to the patient's neck by a clinician, and subsequently, algorithms autonomously extract measurements obtained from the sensor at pre-programmed discrete intervals. A monitor automates this measurement process and records the resulting trends for use by medical professionals. In some examples, the measurements are sent directly to record management systems.

Figure 1:
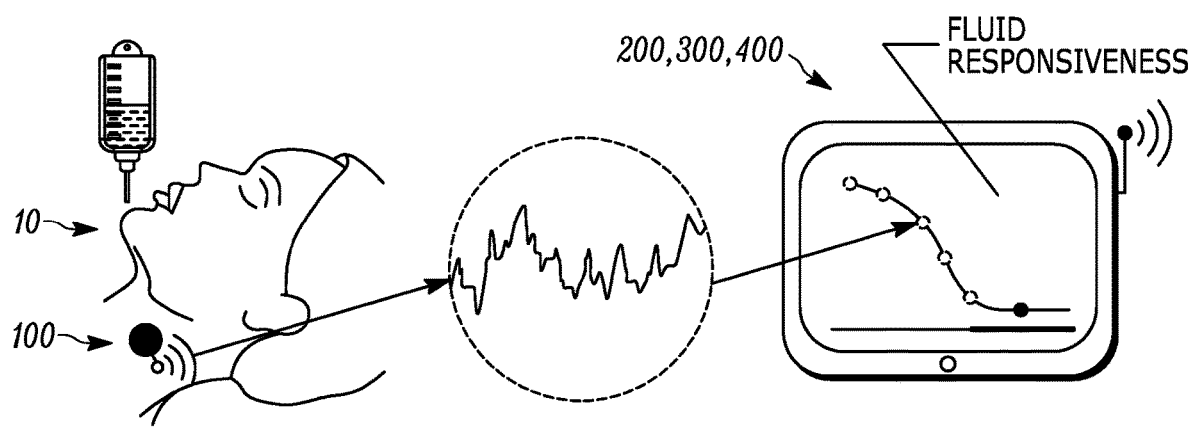
FIG. 1 illustrates an example automated ultrasound system configured to non-invasively monitor fluid responsiveness in accordance with various embodiments.

Turning to the drawings, FIG. 1 illustrates an example automated ultrasound system 10. The system 10 includes a number of sub-systems: the sensor 100 which can be attached to the side of the neck, the ultrasound interface or scanning system 200 to control the sensor and acquire ultrasound data, a signal and image processing system 300 to convert the raw ultrasound data into a measurement that is useful to physicians, and a display 400 to relay the current measurements and measurement history to trend the data. In these examples, the display 400 may be either a stand-alone unit, integrated with an existing bedside patient monitor system, or the data could be sent directly to the patient's electronic medical record for storage and display. Further, it is understood that any number of the scanning system 200, the processing system, and the display 400 may be provided in a single unit (as illustrated in FIG. 1.

Generally speaking, the sensor 100 includes one or more ultrasound transducers, or composite structures having any number of elements, built into a housing. The transducer can include a protective/acoustic impedance matching layer to promote acoustic coupling between the element and transmission medium, a backing material to mitigate unwanted artifacts, and any additional electronic components used to remove any unwanted reactance. The sensor 100 also can include a sensor head, or a structure that houses the transducer and other electrical and mechanical components to enhance the functionality of the transducer, for example, by providing control and monitoring of spatial orientation. A probe is generally defined as an enclosure inside which the transducer is located along with the associated electrical connections.

Ultrasound transducers can be divided into the broad categories of therapeutic and diagnostic ultrasound transducers. Therapeutic ultrasound transducers are adapted to introduce sufficient energy into a tissue volume to bring about some permanent change in its properties. In contrast, a diagnostic transducer aims at only interrogating a tissue region using as little energy as possible to elicit measurements of its properties, but otherwise brings about no long-term changes in the tissue. Diagnostic ultrasound transducers are typically designed for obtaining information from a specific body region, for example: low-frequency (1-5 MHz) sector probes can obtain data from deep within the abdomen, but provide poor information in the tissue near the surface of the transducer. Therefore, higher-frequency (6-12 MHz) linear probes have been designed to elicit more detailed information from shallower regions of the body and are typically termed vascular probes. Other specialized probes also exist for accessing orifices in the human body to allow the higher quality images to be obtained of certain structures than extracorporeal probes would allow, for example transesophageal, transrectal and transvaginal probes are available. There are also a number of invasive catheter probes for obtaining images and measurements within the lumen of blood vessels, the heart and other internal structures. This present system is directed to the use of vascular ultrasound probes for non-invasive extracorporal applications.

Diagnostic transducers can be further categorized into transducers used for creating images and those not used for creating images. For example, single element transducers can be used to measure a Doppler frequency shift induced in a reflected acoustic wave in order to measure blood flow velocity. Since the Doppler frequency shift is angle dependent, some strategies also exist that utilize two or three single-element transducers to obtain an angle-independent measure of the blood velocity in a vessel. However, in these types of sensors, no image generation is performed. Conversely, transducers for image generation can be categorized by the number of active elements (genesis points for the acoustic compression wave) and method of focusing used to create beams of ultrasound energy. Ultrasound beams for imaging can be generated either using a mechanical focus (usually applied to the surface of single-element piston type transducers) or electrically focused by adjusting the phase shift of the signal applied to and elicited from a multi-element transducer. For image generation, the former strategy requires a method to translate the transducer in order to create the image. The latter case typically requires 32 or more elements arranged linearly with a few fractions of a millimeter space between each element in order to successfully perform the electronic steering and focusing required to produce a useable image.

Figure 2A:
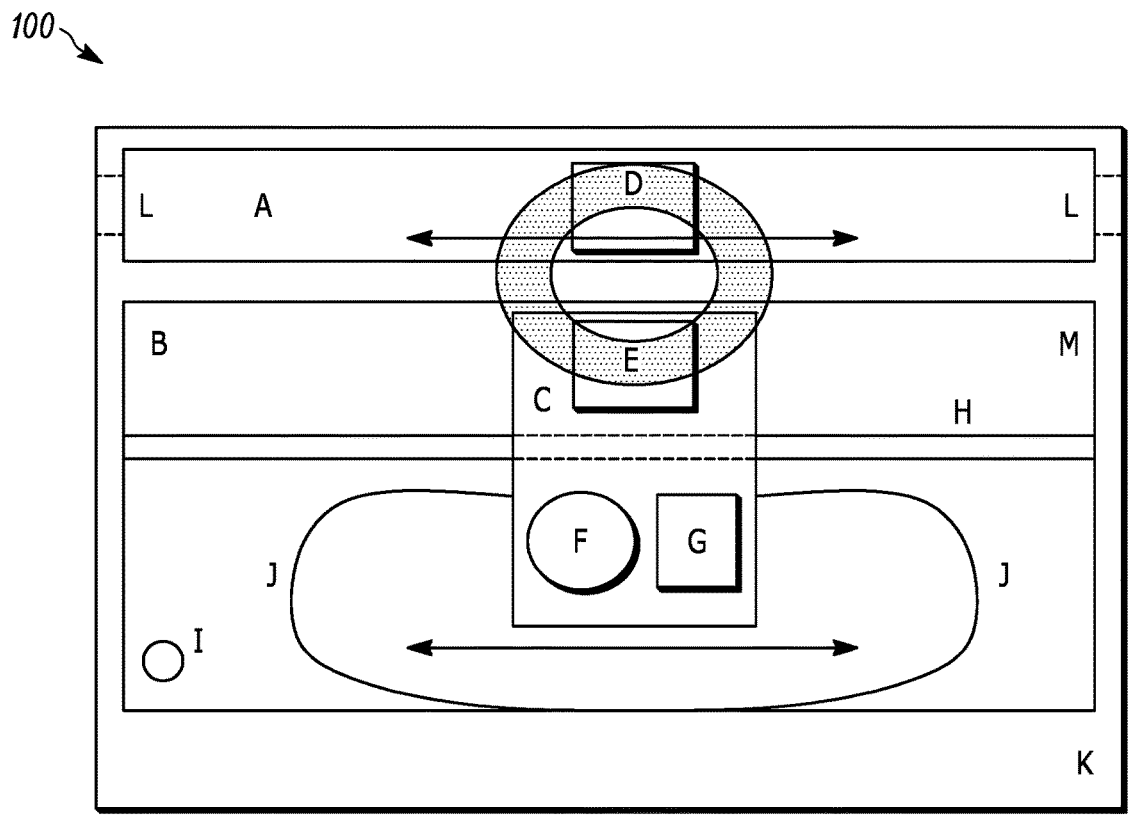
FIGS. 2A and 2B illustrate an example schematic of a wearable ultrasound sensor of the automated ultrasound system of FIG. 1 in accordance with various embodiments.
Figure 2B:
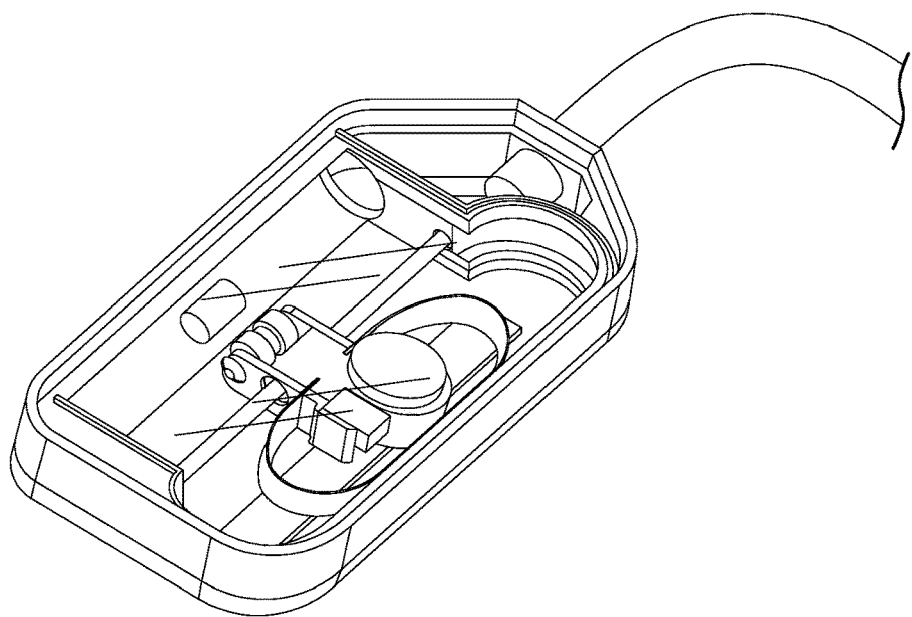

As illustrated in FIGS. 2A and 2B, an example sensor 100 includes a low-friction, high-speed pneumatic actuator that includes a permanent magnet (D), a tube guide body (A), a low-friction lubricant or coating to limit air leaks and minimize stick-slip effects between the magnet D and actuator body (not shown), and any number of hard or soft stops to prevent excursion of the magnet from the tube guide body. The actuator further includes sealed attachment points for the tubes to supply and remove air from the actuator.

The sensor 100 also includes a sealed reservoir (B) that contains a sensor head (C) including a support structure that contains an ultrasound transducer (F), an optional position encoder (G), a magnet or ferromagnetic material to couple forces generated by the actuator to the sensor head (E). The sealed reservoir further includes durable and flexible wires allowing the moving scan head to communicate with the stationary inner wall of the reservoir (J), a low-viscosity acoustic coupling medium to couple the acoustic wave from the ultrasound transducer to the acoustic window (M), an optional guide rail to facilitate the smooth translation of the sensor head through the reservoir (H), a port in the reservoir allowing filling or draining of the acoustic coupling medium (I), and an acoustic window on the upper or lower wall of the reservoir (not shown) enabling the longitudinal acoustic wave to escape the reservoir to enter the patient through a suitable external coupling medium (i.e. ultrasound gel or water). The acoustic window can be on the upper (out of the page) or lower (into the page) side of the sensor. The sensor head moves within the fluid reservoir parallel to the acoustic window. The fluid allows the acoustic waves to pass from the sensor head through the fluid and enter/exit the acoustic window. The gel pocket may facilitate acoustic coupling. In some examples, the pneumatic actuator may be located within the reservoir. The ultrasound and associated electronics may be integrated with the sensor body to provide a wireless solution.

Additionally, the sensor 100 can include an adhesive covering/coating, strap or band that can be used to attach the sensor to the patient at an appropriate location (not shown). The adhesive covering or coating can be a disposable component which secures the sensor to the patient's neck and provide a coupling medium between the sensor and the skin of the patient.

The sensor 100 can rely on the dynamic magnetic coupling (M) between the pneumatic actuator (A) and a sealed reservoir (J) containing the ultrasonic transducer. A magnet in both regions or a magnet and a ferromagnetic material are aligned so that a continuous magnetic circuit is formed where an attractive force is generated that attempts to continually minimize the magnetic field path length. When the magnet in the actuator moves, the field lines will be "stretched" and the sensor head magnet will compensate by following the actuator magnet to minimize the elongated magnetic path length. This magnetic effect may also makes it possible to omit the guide rail (H), in some examples.

In some examples, the pneumatic actuator may be designed with a known gas leak rate in order to provide a gas bearing effect to minimize friction and/or to reduce manufacturing tolerances to facilitate more rapid and cost-effective production. Additional magnets or ferromagnetic materials may be applied in close proximity to the pneumatic actuator's magnet to limit the normal force's influence on the actuator friction in the tube guide body as well as the sensor heads friction on the guide rail.

It is understood that in some examples, the guide rail (H) may be omitted and the sensor head allowed to slide along the body of the pneumatic actuator. The guide rail may also be rotated or translated in order to adjust the angle of the sensor head relative to the surface of the skin in order to obtain a perpendicular image, slightly off perpendicular image to minimize reflections or capture images across multiple planes in order to measure vessel/flow trajectory or build 3D images of a segment of tissue.

In some examples, a single air supply inlet may be used to replace the differential air supply. To actuate the mechanism, a pressure-vacuum profile or a spring return with a positive only pulsed pressure source may be used. A compressed, electrically or chemically generated air source may be integrated with the sensor body so that no air hoses are required.

In some forms, the pneumatic actuator, guide rail and associated structures may be designed to have a rigid curvature to provide an improved fit for patient body areas. However, in other forms, the pneumatic actuator, guide rail and associated structures could be manufactured from flexible/compliant materials to allow the curvature of the sensor to be adapted to a variety of patient body areas.

The sensor may be designed to perform photoacoustic imaging by selecting an appropriate ultrasound transducer and integrating a suitable photoacoustic light source. Similarly, bioimpedance/skin conductivity electrodes, ECG, temperature, pulse oximetry sensors could be integrated with the sensor body to provide a multi-modal physiologic monitoring capability.

In an example, a single-element ultrasound transducer with a mechanical focus could be used to collect imaging data. Further, the single-element transducer may be replaced with an annular array transducer allowing the focus to be adjusted along the beam to optimize the image resolution at a particular depth. Compound imaging may be employed by adding a "wing" structure and revolute joint to the sensor head to create a predefined tilt of the transducer co-planar to the image plane. The opposite angular shift could be designed to occur in the opposite direction of motion. The two images of the same structure obtained from two slightly different angles could be combined to form a single image. The quality of the resulting image would be expected to reduce speckle noise, clutter and other artifacts common to ultrasound imaging. Clinical experience suggests that real-time spatial compound imaging can improve contrast and resolution, thus providing improved images of peripheral blood vessels.

A multi-element array (i.e., piezoelectric—PZT or capacitive micro-machined ultrasound transducer—CMUT) can also be used to replace the single-element transducer and images generated using an advanced synthetic aperture ultrasound approach, where an electronically steered beam is swept through the imaging plane from a series of source positions controlled by the actuator motion. This technique has the ability to boost the resulting image resolution and quality and may be useful in achieving improve image quality with fewer transducer elements.

Figure 3:
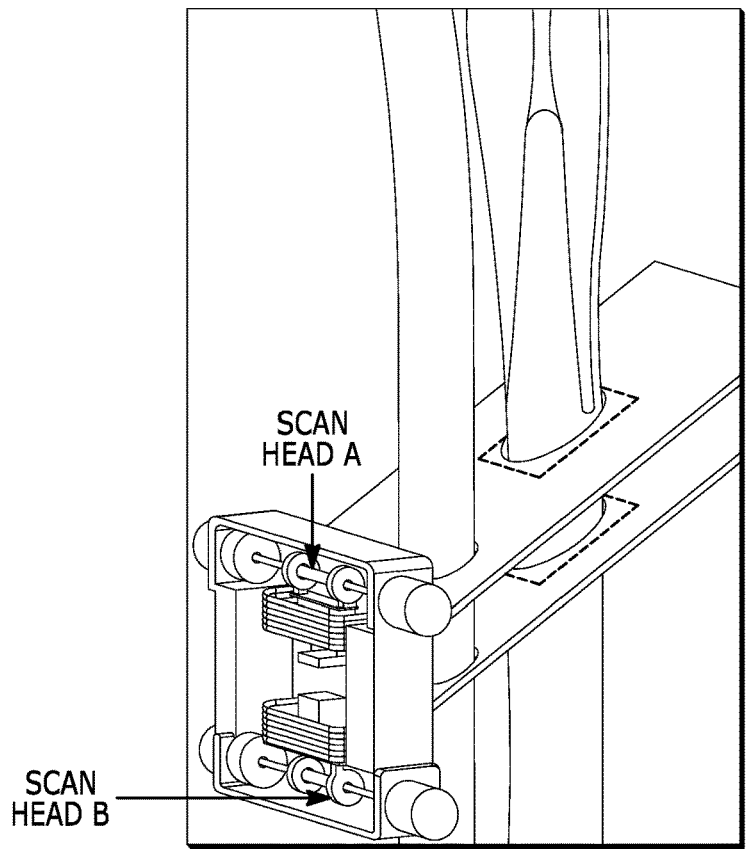
FIG. 3 is a perspective view of an example wearable ultrasound sensor having a secondary sensor head and actuator of the automated ultrasound system of FIG. 1 in accordance with various embodiments.

As illustrated in FIG. 3, a secondary sensor head and actuator that can be incorporated to allow three measurement modes to be realized. The first mode would simultaneously obtain B-scan images from two adjacent parallel planes, as shown in FIG. 3. From these data, vessels may be located along with their geometric changes over time and their trajectory relative to the surface of the skin computed. For the second mode, one of the parallel planes could switch from B-scan mode to flow measurement mode to obtain the blood velocity versus time, using the vessel trajectory computed from the first mode to compensate for geometric and flow signal distortions due to the angle between the US beam and vessel lumen. During this process, the remaining B-scan plane will track vessel position and geometry to compensate for motion artifacts and compute vessel cross-sectional area changes as a function of blood flow. In order to avoid the assumption of parabolic flow, a third mode of the sensor will measure the blood flow profile spatially across the vessel lumen at discrete points and use this data to build a flow model that can be used instead of assuming parabolic flow. With two imaging planes positioned suitably close together, the correlation of the speckle due to the blood flow between each plane could be used to measure the velocity of the blood flow.

Figure 4A:
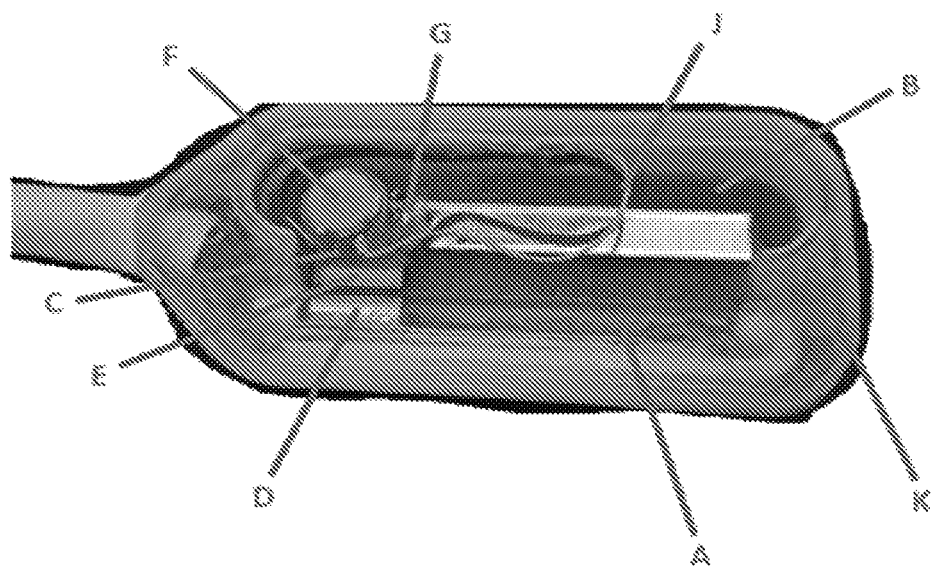
FIG. 4A is an example wearable sensor and bed-side monitor having an external pneumatic actuator in accordance with various embodiments.

FIG. 4A illustrates an example transducer that uses a fused quartz tube as the tube guide body, and to provide a smooth surface along which a permanent Neodymium Iron Boron (NIB) magnet could slide. The corresponding elements from FIG. 2A are labeled. To further reduce friction and improve sealing, the magnet was encased in a paraffin wax plug. However, it is understood that other more durable materials, such as Polytetrafluoroethylene or even aluminum, could be used. A second NIB magnet was integrated into the sensor head. The force in the direction of motion experienced by the sensor head is supported by a small fused quartz rod on which the sensor head can slide. A quadrature optical encoder is integrated with the sensor head to provide position information to the control system by sensing the gradations on the reflective strip adhered to the inside wall of the reservoir. A single-element ultrasound transducer with a mechanical focus was used for the probe prototype.

Figure 4B:
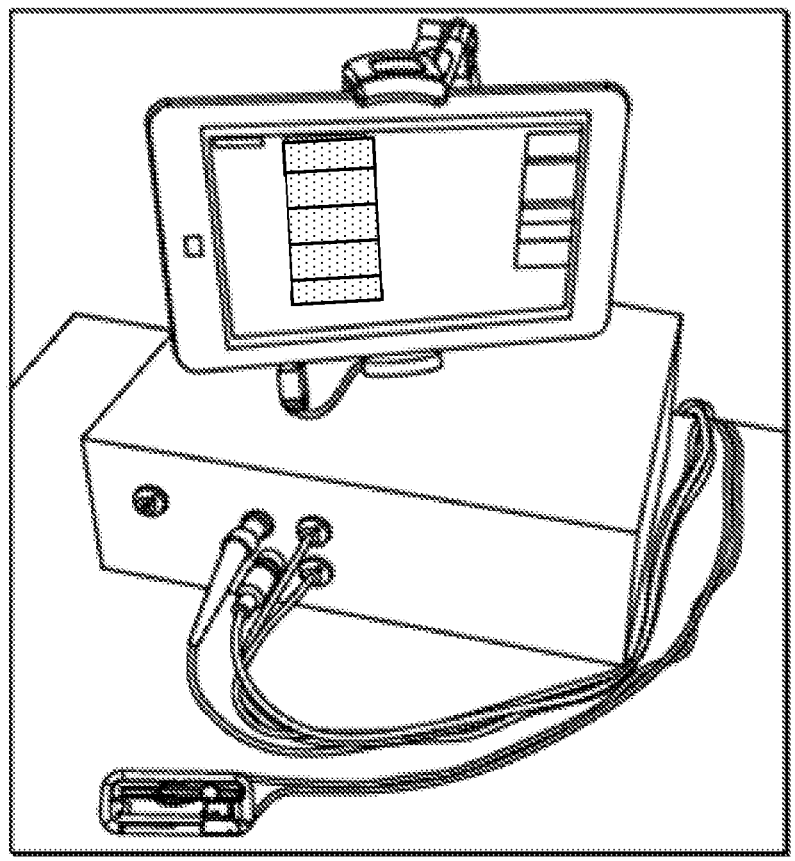
FIG. 4B is an example bed-side monitor prototype in accordance with various embodiments.

FIG. 4B illustrates an example display 400 that collects data from the transducer using standard B-scan ultrasound imaging hardware. This probe design utilized the differential pressure approach, where a high-speed electro-mechanical valve was used to alternately switch the pressure source from one end of the actuator tube guide body to the other end, while simultaneously venting the opposite end to the atmosphere. A basic control system was developed that would switch the pressure once the sensor head had moved a specified location within the probe body. Because a finite amount of time is required for the sensor head to decelerate and change direction, the controller had to take the direction of motion into account to prevent double triggers of the valve.

Figure 4C:
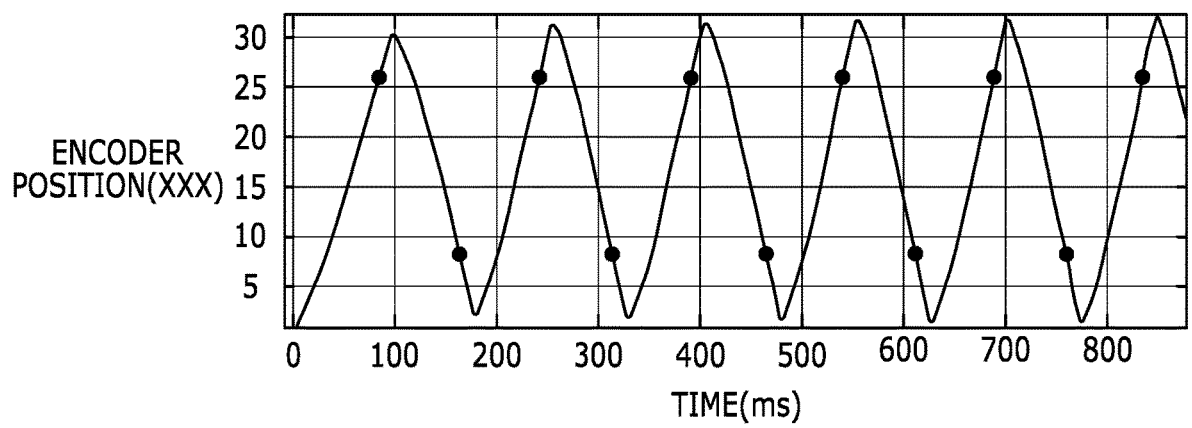
FIG. 4C is an example quadrature optical encoder measurement depicting sensor head position versus time in accordance with various embodiments.
Figure 4D:
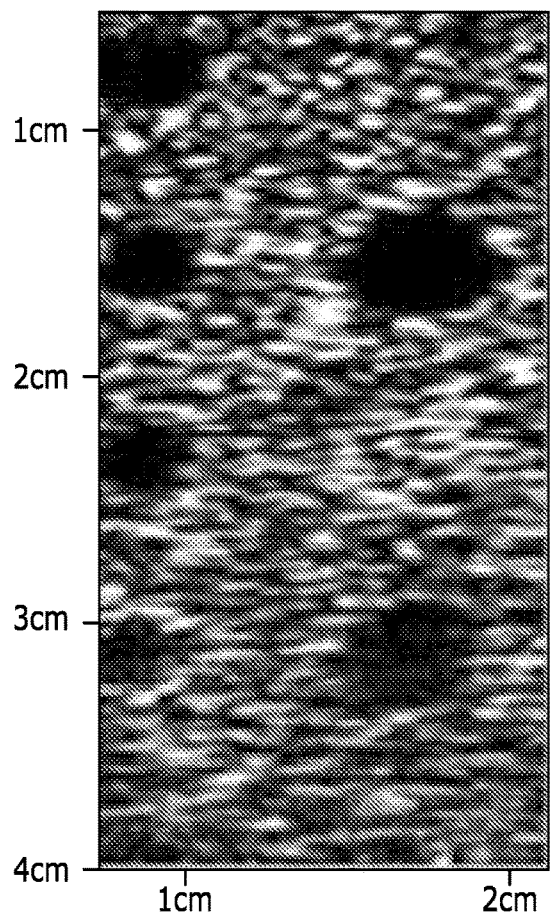
FIG. 4D depicts a single image frame collected from an ultrasound phantom in accordance with various embodiments.
Figure 4E:
FIG. 4E is an example image of an internal jugular and common carotid artery from a healthy volunteer captured by a wearable sensor, the diameter change tracked versus time and the contractility index computer from these data in accordance with various embodiments.

The resulting scan head positions over time are illustrated in FIG. 4C. The markers indicate the point at which the valve was triggered to allow the sensor head to switch direction. These data were collected in the fully assembled sensor in which the sensor head was sealed with acoustic matching fluid. Despite drag effects it can be seen that a frame rate of approximately 15 fps was achieved. While experimentation with higher pressures was not performed, it is conceivable that higher frames rates could be achieved using this technique. With reference to FIG. 4D, after the sensor operation and dynamics were evaluated, the probe collected B-scan data from a calibrated laboratory ultrasound phantom. The anechoic cysts are clearly visible within the surrounding speckle. Thereafter, images of the internal jugular and common carotid artery from a human subject were collected as illustrated in FIG. 4E.

The IJ is a thin-walled compliant vessel that adjusts to the volume status of the body by changing its diameter depending on the total body fluid volume. This vessel contracts and expands with each respiration. Negative pressure created by the inspiration of the patient increases venous return to the heart, briefly collapsing the IJ. Inversely, the increased pressure created by exhalation decreases venous return to the heart and the IJ diameter increases back to its baseline diameter. Additionally, by monitoring the IJ characteristics over time, internal fluid status (loss/gain) and whether a patient's vascular system is responding adequately to a fluid bolus can be detected from the changes in the IJ geometry. Moreover, serial measurements of IJ properties can be used as a marker for response to treatment, early detection of volume depletion, and prevention of over-hydration.

Figure 5:
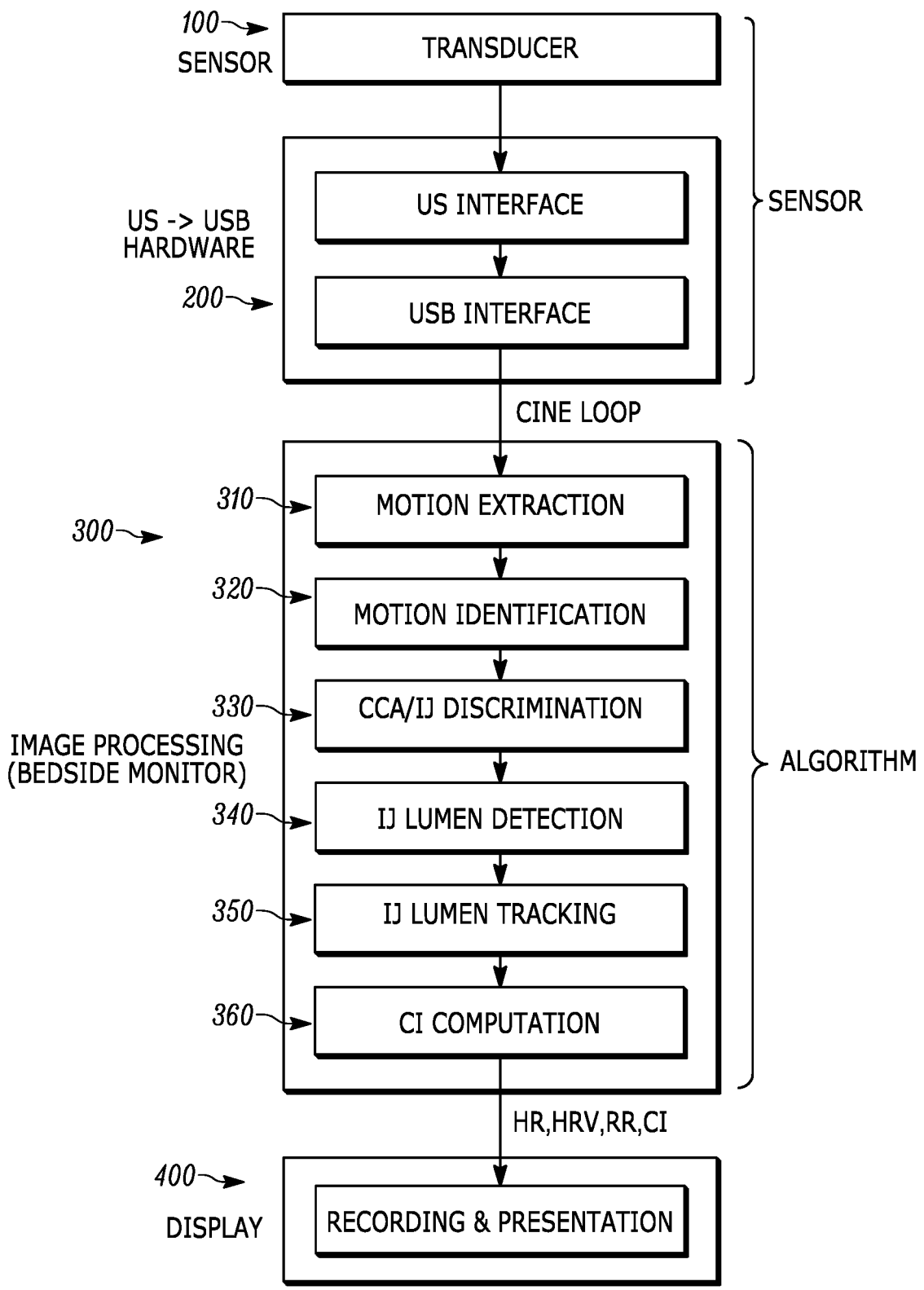
FIG. 5 is a flow chart illustrating the automated ultrasound system of FIG. 1 in accordance with various embodiments.

With reference to FIG. 5, a flow chart describes the system 10. First, the sensor 100 cooperates with the scanning system 200 to orientate and acquire low-level US data. At least one of 1-dimensional A-lines, 2-dimensional planes, and 3-dimensional volumes may be automatically acquired.

Generally, the processing system 300 utilizes a swarm speckle tracking approach enhanced with motion power analysis and "friction-lock" algorithms to automatically identify regions from which tissue motion is originating to determine the presence or absence and respective locations of vessels such as the IJ and CCA. The term "swarm" refers to a multitude of ROI firstly being indiscriminately dispersed across the ultrasound image. No specific pattern or placement is required so long as there is an even distribution or approximately even distribution. The ROI are then encouraged to migrate away from sources of unstable speckle and gather around regions of stable speckle in a similar manner to how ants swarm around a source of nourishment.

Subsequently, the processing system 300 identifies the vessel wall regions of the respective vessels by applying a "shoreline detection algorithm," and then automatically determines the optimal positions at which to apply tracking markers at periodic points around the speckle field representing the vessel, and then tracks movement of each marker.

The processing system 300 automatically initiates the measurement sequence, computes a contractility index based on the temporal geometric changes due to heart rate or respiration rate by applying math functions to the markers. Accordingly, diameter, circumference, and cross-sectional area of the vessel can be computed for each plane or volume obtained. These measurements may be taken along a cross section of the vessel. Motion artifacts and pulsations due to the heart beating are automatically removed and the ratio between the maximum and minimum of the measurements as a function of respiration is calculated.

Figure 6A:
FIG. 6A is a speckle swarm motion extraction algorithm showing initial conditions with a sparse matrix assignment 1 in accordance with various embodiments.
Figure 6B:
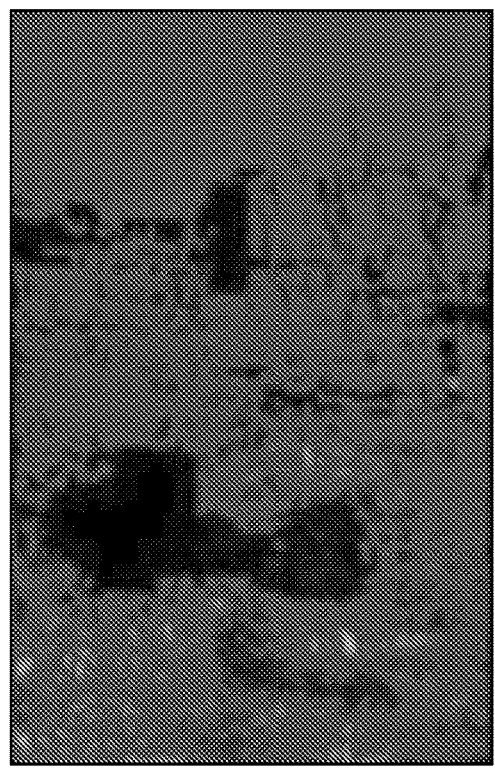
FIG. 6B is a speckle swarm motion extraction algorithm showing end conditions after initially starting with a dense matrix over the duration of the cine loop in accordance with various embodiments.

With continued reference to FIG. 5 and the process steps performed by the processing system 300, at step 310, motion features are extracted from cine loop. As previously stated, the processing system 300 extends the speckle tracking technique beyond the typical elastography applications to enable the measurement of tissue kinematics for the detection of cyclic motion signatures from US cine loops. The processing system 300 monitors the relative motion of a swarm of tracking markers, which enables the kinematic information contained in cine loops to be extracted. An example is presented in FIGS. 6A & 6b, where the original cine loop is overlaid by a square matrix of markers. Markers falling in areas of tissue with high echogenicity and a persistent, unique speckle pattern can track any associated tissue motion. However, markers falling within the vessel lumen will experience a rapidly changing speckle pattern due to the flow of blood. A gentle pull force vector was randomly assigned to migrate "low-correlation" markers to the walls of the vessel, as shown in FIG. 6B.

Once the markers have all attached to "trackable" regions in the image, any tissue or image motion will be captured by the marker motion. In this example, tracking was performed on the processed B-mode image; however, a similar process could be performed on the underlying RF data. As with traditional speckle tracking, a region of interest (ROI) and a search region is defined around each marker co-ordinate. Between successive frames any change in the position of the ROI can be identified by searching for the highest correlation position of the ROI in the search region. This allows the marker (center of ROI) to track tissue displacement. Therefore, in our swarm tracking approach after processing a cine loop, a matrix of x and y co-ordinates defines the spatial position of each marker for each image frame. Thereafter, a frame to frame displacement (velocity) vector for each marker was computed using the processing system 300. In the ideal situation, tissue exhibiting oscillatory motion will produce a sine wave, whereas stationary tissue will produce a flat response. However, tissue deformation is typically a complex process requiring the next phase of the algorithm to specifically identify this motion.

In summary, step 310 includes applying a matrix of tracking markers over cine loop B-mode/B-scan data; applying a low intensity random force vector on each tracking point that will allow it to migrate to a distant location should a consistent region of correlation (speckle) exist. If no speckle is available to lock in to, the tracking point will continue to migrate until it attaches to a region with stable speckle signature. Next, a region of interest perimeter is defined around each point, and a search region perimeter around each region of interest is also defined. Last, step 310 computes the vector describing the frame to frame spatial displacement between each tracking point over the complete cine loop sequence by computing the minima of the cross-correlation between the region of interest at each location within the search region.

Next, at a step 320, the processing system 300 detects regions of periodic motion from the marker vector data. Subsequent path analysis of the maker motion can automatically identify regions exhibiting periodic motion, such as the motion due to vessel pulsations, or regions of unstable speckle due to blood flow. This provides a convenient way for algorithms to "see" the motion contained in cine loops to automate US measurements. To achieve this, the Euclidian distance (or distance along a specific axis) of each marker's velocity vector) can be computed frame to frame and stored. Angular filtering can be applied to increase the sensitivity of the algorithm to motion in a certain direction.

Figure 6C:
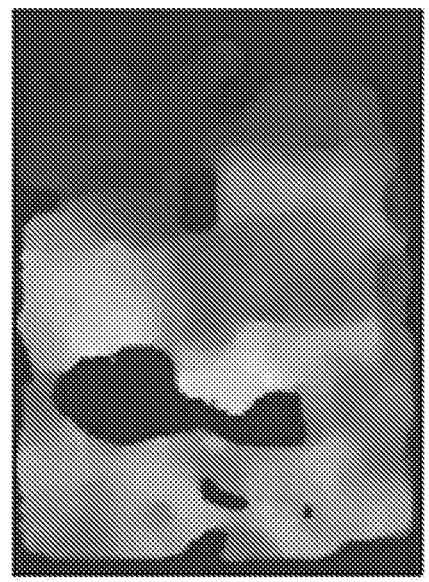
FIG. 6C is an example of a speckle swarm motion extraction algorithm showing a spatial power spectral density map indicating motion regions in accordance with various embodiments.
Figure 6D:
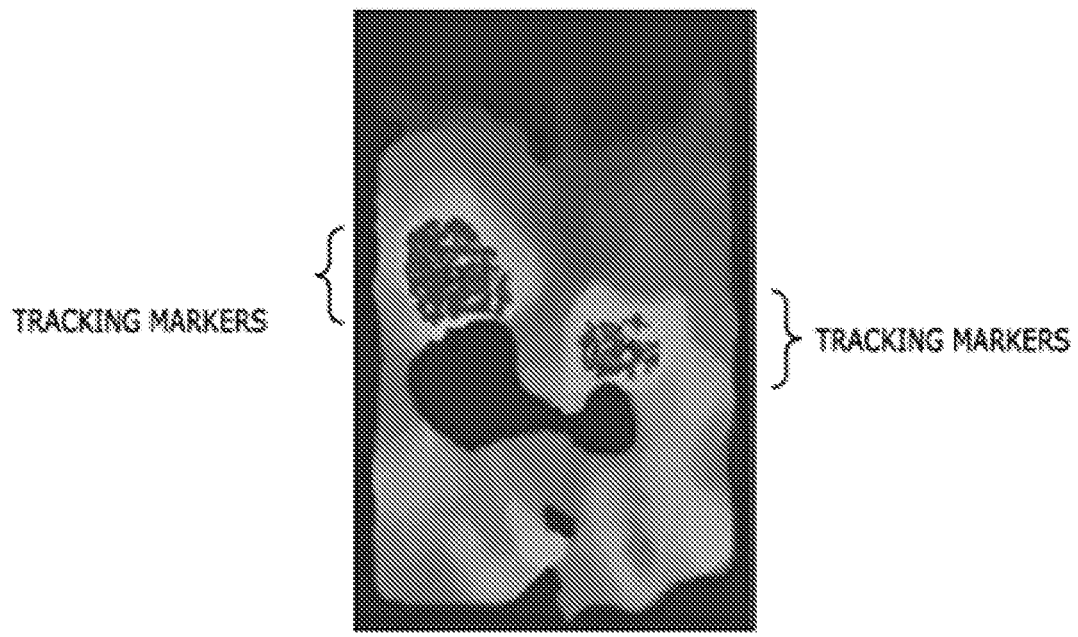
FIG. 6D is a speckle swarm motion extraction algorithm showing tracking markers identified within motion regions in accordance with various embodiments.

The resulting data can be band pass filtered to remove any low frequency motion artifacts, leaving only frequencies in the physiologic range of interest (0.5-5.0 Hz or 50-300 BPM). A short-time Fast Fourier Transform (sFFT) can then be applied and the power spectral density (PSD) of the spectrum computed. FIG. 6C illustrates the spatial PSD after appropriate linear scaling and color mapping, which clearly identified regions of periodic motion. Regions of motion can be seen to border on both vessels due to their pulsations. The light regions represent greater motions compared to the darker regions. A 3D peak detection algorithm can then be applied to the spatial PSD map to detect sources of tissue motion. One possible implementation of the peak detection algorithm is applying a threshold-based search function that generates a ranked list of connected areas in the resulting binary image versus threshold which fall within a specified range of areas. The first two peaks in a typical cine loop with CCA and IJ will ideally represent the vessel wall motion. The tracking markers that fall within the two motion regions can then be selected as shown in FIG. 6D.

In summary, step 320 includes the steps of computing Euclidian norms (or motion along beam axis) of all time domain position vectors and compensating for motion by extracting the hemodynamic motion artifact from the position vectors using an infinite impulse response (IIR) zero-phase digital band-pass filter with 3 dB Pass-band points at 0.3-4.0 Hz and stop-band 3 db points at 0.1 and 6.0 Hz with 3 dB pass-band attenuation and 30 dB stop-band attenuation. For each tracking point, the processing system 300 computes the short-time Fourier transform (sFFT) and the PSD representing the sFFT. The process 300 applies a 3-dimensional peak detection algorithm to identify first two spatially separated regions in resulting binary threshold image. Last, tracking markers are selected that fall within detected peak regions.

Figure 7A:
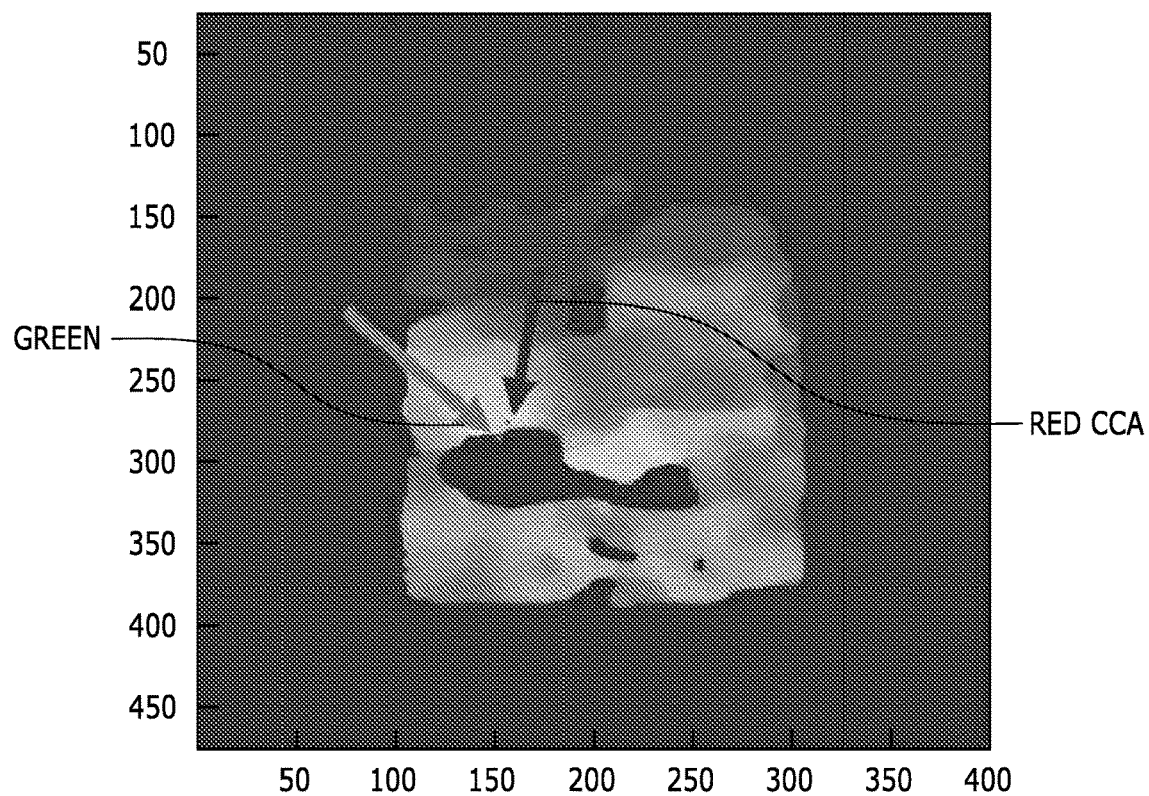
FIGS. 7A and 7B illustrate an example comparison of tracking markers falling within the CCA and IJ motion regions, respectively, and the resulting phase shifts obtained from healthy control data in accordance with various embodiments.
Figure 7A:
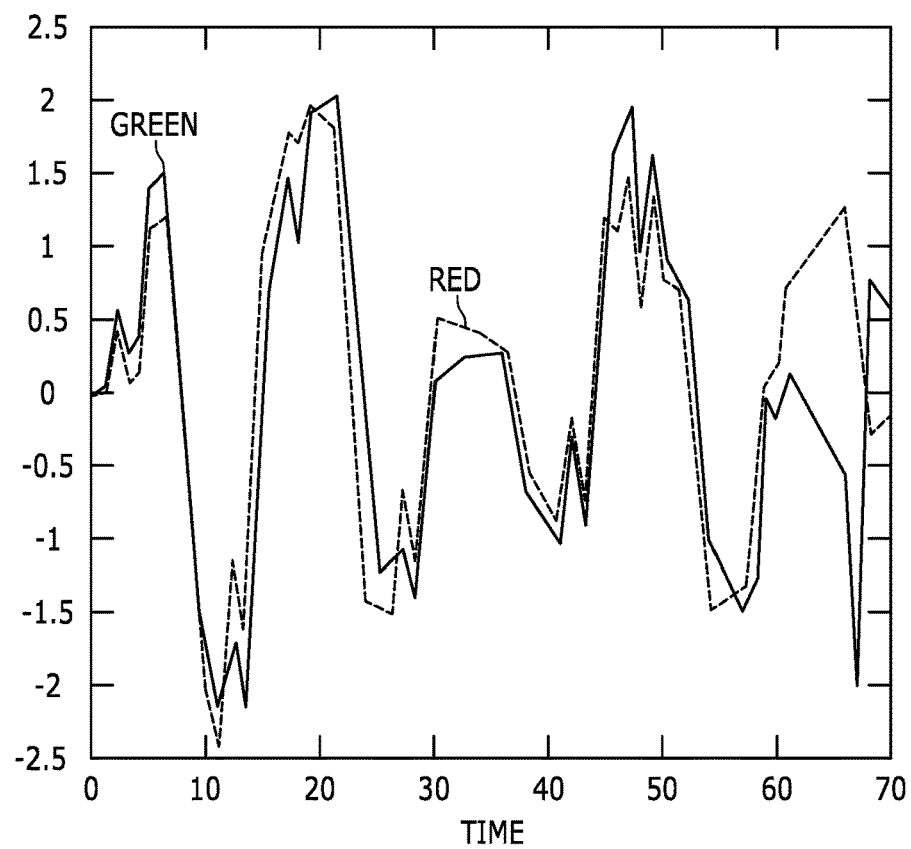
Figure 7B:
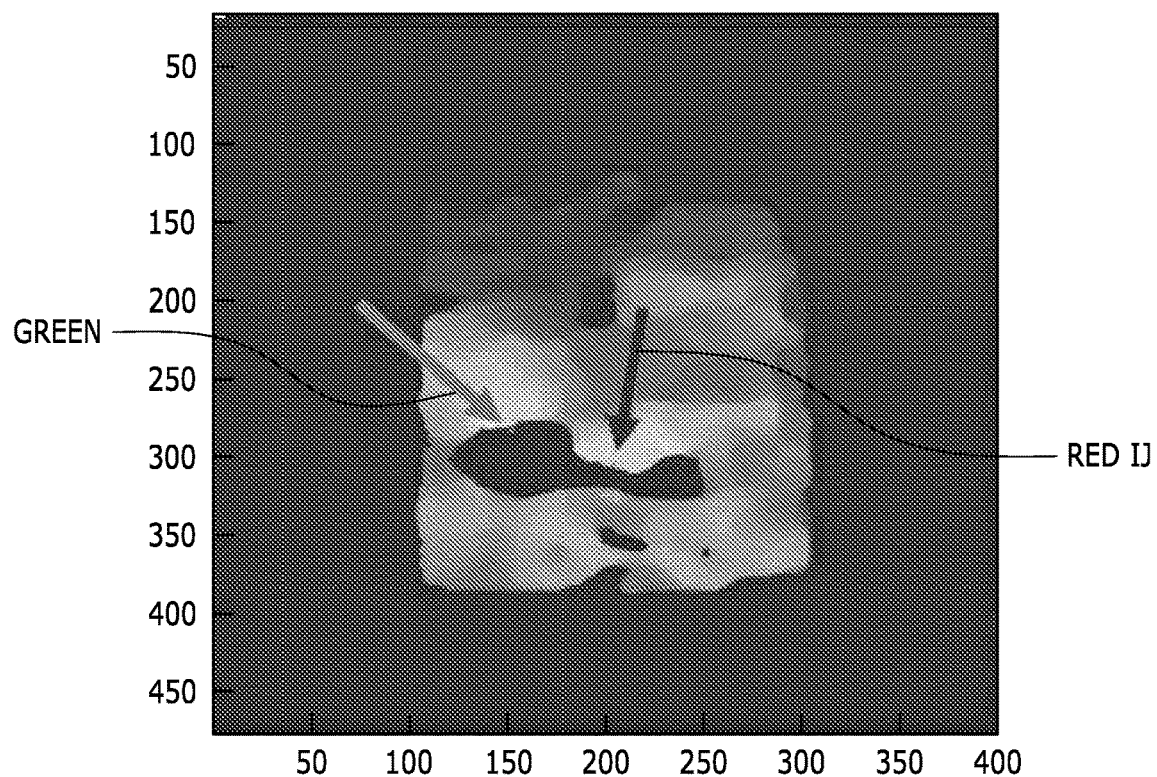
Figure 7B:
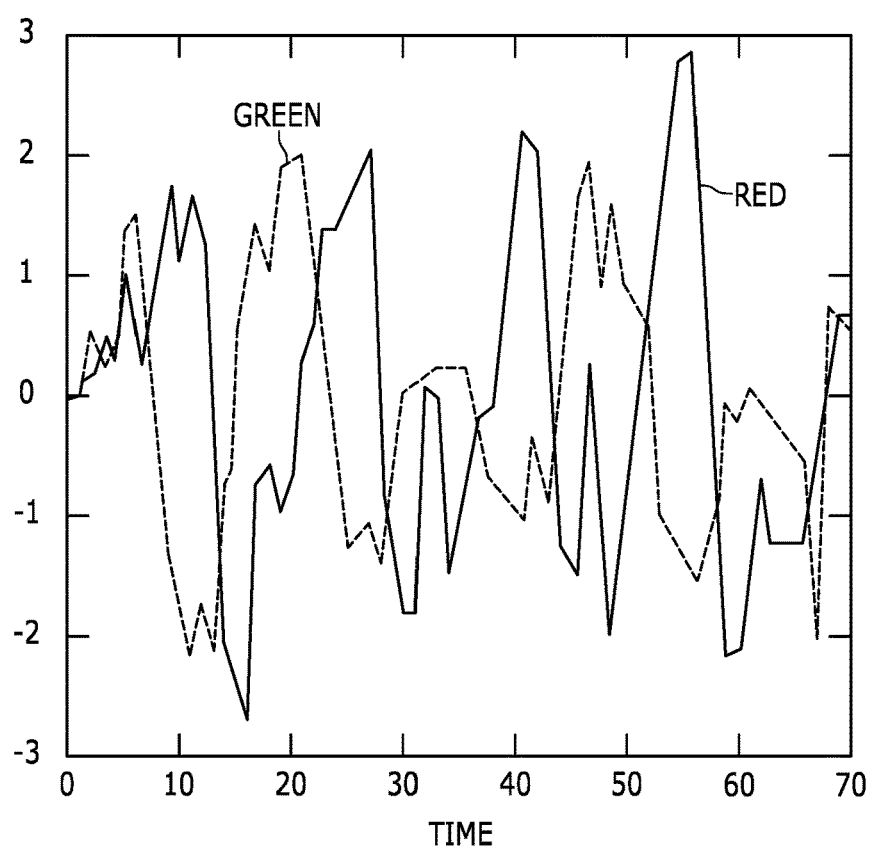
Figure 8:
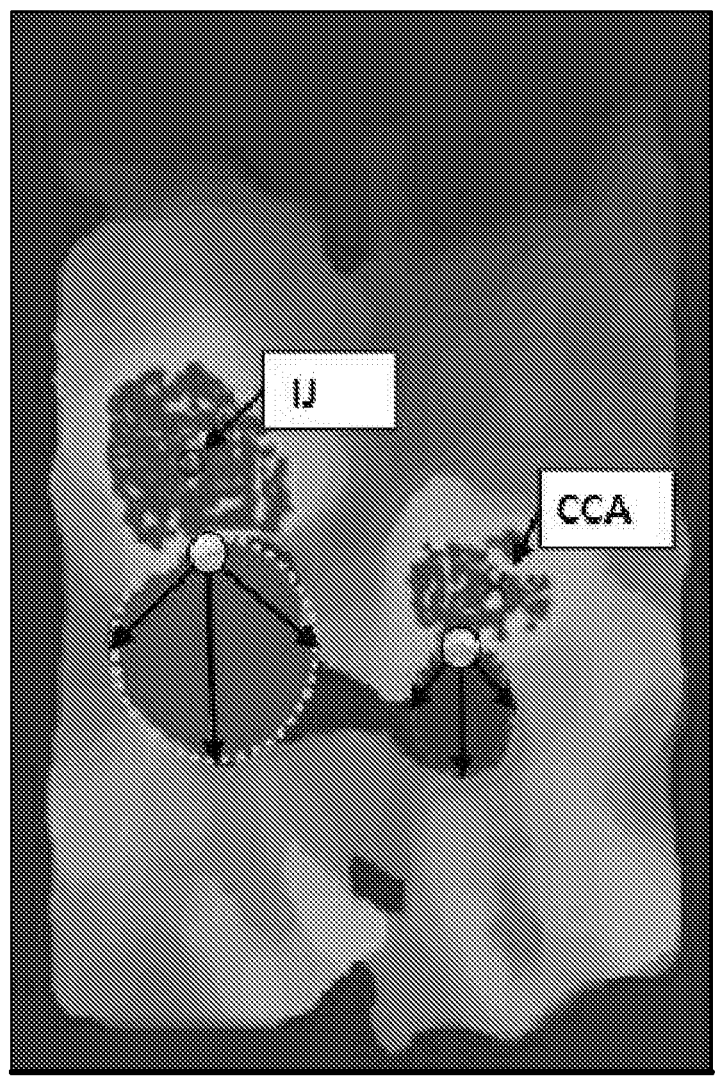
FIG. 8 illustrates a process for detecting the IJ lumen in order to fit a line segment or a spline to track geometric changes in the cross-section of the vessel over the cine loop in accordance with various embodiments.

Next, at a step 330, the processing system 300 takes that the motion signatures from the IJ and common carotid artery (CCA) and interrogates them to differentiate the CCA and IJ vessels. By observing human subject data, it was determined that pulsations in the IJ and CCA are not in phase. The motion profiles of individual tracking markers can be compared between motion regions or the means or medians of the motion profiles exhibited in the regions can be compared. By computing the correlation (if mean/median is used) or covariance matrix between the tracking marker motion paths that fall within the regions encompassing peak power spectral density, the motion occurring in a region can be classified as either moving in-phase or out-of-phase. Due to vascular mechanics, the CCA motion signature will exhibit a phase shift compared to the IJ and can be used to differentiate the vessels. A comparison of tracking markers falling within the CCA and IJ motion regions and the resulting phase shifts obtained from healthy control data is illustrated in FIGS. 7A and 7B, respectively. The phase shifts corresponding to different 'colored' tracking makers for the CCA are labeled in FIG. 7A. Similar labeling is done in FIG. 7B for the IJ.

An alternate method for the discrimination of CCA versus IJ may include the use of Doppler to assess blood flow direction. However, for this method an angle is required between the blood flow and ultrasound beam, which would deform the geometry of the vessel if the same transducer was used for the geometric measurements. Furthermore, motion of the vessel out of the imaging plane will result in greater speckle changes than in-plane motion, which will degrade the quality of the tracking algorithm.

In summary, step 330 includes selecting tracking markers to compare or compute mean/median of markers in peak regions, computing cross-correlation between motion profiles to determine motion phase shift, cluster tracking markers according to phase shift, computing centroid of clusters and then labeling each cluster according to phase as CCA and other as IJ.

Next, at a step 340, the processing system 300 identifies IJ/CCA lumens so that line segment(s) or a spline can be fitted and length(s)/area computed to track geometric changes in the cross-section of the vessel over the cine loop. A diagram of this process is provided in FIG. 4. Due to the pull vector, regions with unstable speckle, such as those in vessel lumen, will be void of tracking markers resulting in sparse regions of the quantized spatial distribution maps representing tracking marker distribution (dark blue). Regions of identified tissue motion corresponding to the identified IJ will fall adjacent to these sparse regions allowing a segment along the edge of the vessel to be easily identified. The center of this line segment will form the genesis point (partially transparent small white circles between marker cluster and void) for a circular spline that will fit using a suitable algorithm (i.e. least squares, genetic algorithm, etc.) to maximize its area, but minimize the overlap with the number of markers (motion regions) the area contains.

In another example implementation of step 340, an alternate strategy for detecting the vessel lumen is to evaluate the frame to frame correlation of the speckle. Due to the movement of the blood, the speckle present in the lumen of vessels is highly variable and will exhibit a low frame to frame correlation compared to the surrounding tissue. However, this method is limited since any tissue motion or movement artifact will also degrade the frame to frame correlation. Furthermore, it can be challenging even for a skilled operator to obtain a suitable signal to noise ratio within the vessel lumen to obtain both a high-quality vessel lumen measurement. Doppler-based methods may also be used to estimate the vessel wall; however, due to low blood flow at the vessel wall, obtaining an accurate vessel wall estimate can also be difficult.

In another example implementation of step 340, a processing system searches for the best fit of various oval geometries on the image by computing the spatial derivative around the perimeter of an oval using a cost function comprised of the ultrasound image intensity. For example, the processing system may search for a best fit by varying a minor axis, a major axis, rotation, and/or position, etc.) and compute a cost function for each permutation. The peak of the cost function will relate to the best set of oval position and geometry parameters that correspond to an oval closely approximating the IJ vessel wall. In examples, this technique also discriminates the IJ from CCA, as the vessel wall motion of the IJ has a more significant PSD signature than the CCA. It is believed this effect is due to its lower pressure and the non-linear elasticity of the surrounding tissue.

In summary, step 340 includes selecting vessel wall tracking points by identifying the tracking markers falling along the vessel wall border and applying the optimization algorithm to fit linear, oval, spline or other suitable geometric function to the tracking marker void region minimizing the overlap with other tracking markers. That is, in some implementations, the step 340 determines a best fit and determines tracking markers coinciding with the vessel, e.g., tracking markers associated with the vessel wall and vessel wall movement.

Next, at a step 350, the processing system 300 tracks the IJ/CCA lumen. Tracking markers are selected along edge of splines within some tolerance. Using the previously recorded motion path data, these markers will be tracked retrospectively frame by frame. Alternatively, newly acquired data can be collected prospectively to track the markers motion. For each frame the fit of the geometric function is optimized based on the position of these tracking markers. This process is continued over a specified number of cardiac and respiration cycles. Should the error in the final fit exceed a certain threshold, the numbers of markers decrease by a certain amount, or the distribution of the markers along the geometric function fall below a specified threshold, this may suggest the data acquired from the sensor has been disturbed and the vessel detection procedure should be performed again.

In summary, step 350 includes selecting tracking markers that are distributed along a geometric function. For each prior or future frame, the motion of these markers is then computed, and an optimization algorithm is applied to adjust fit of geometric function to accommodate the new marker position. Upon evaluating performance of the optimization algorithm/fit to determine that a reliable measurement has been obtained, the process is then repeated for the next image frame.

Figure 9A:
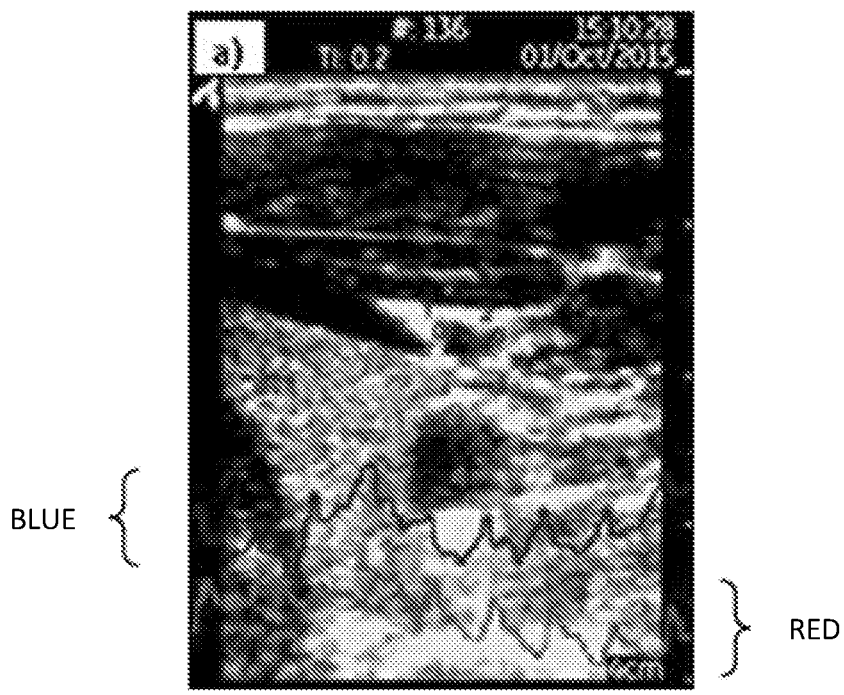
FIGS. 9A and 9B illustrate example measurements from the CCA and IJ using a linear caliper (FIG. 9A) and a spline (FIG. 9B) in accordance with various embodiments.
Figure 9B:
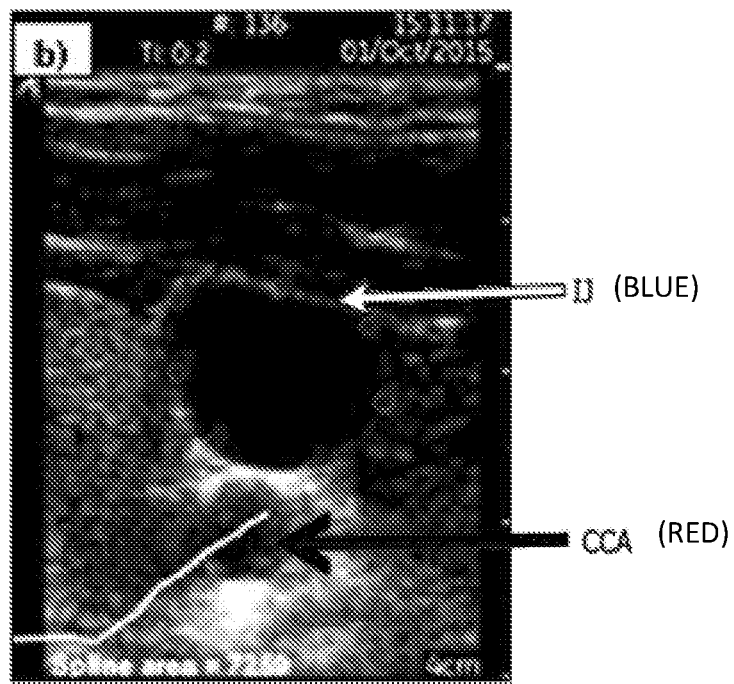
Figure 9C:
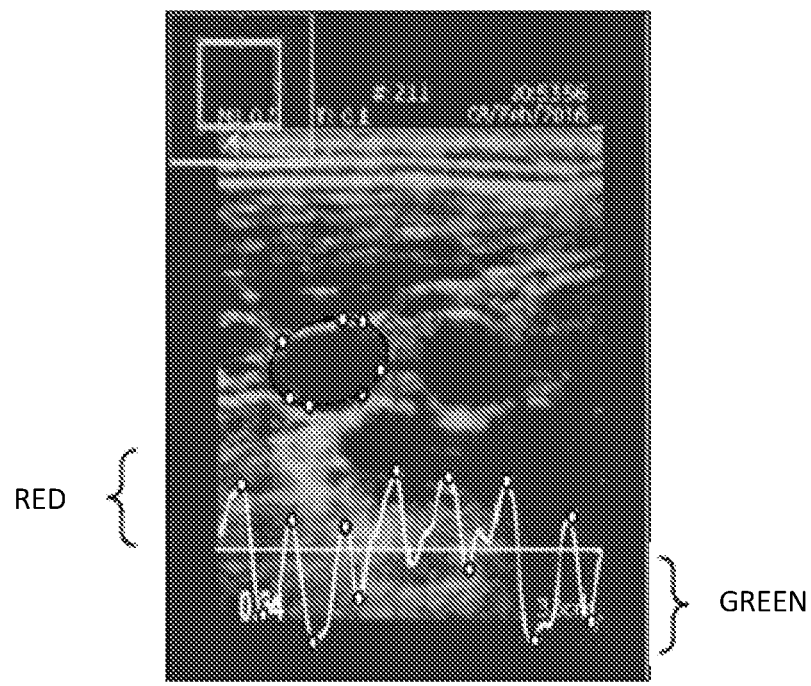
FIG. 9C illustrates another example measurement of a vessel using a spline fitting similar to FIG. 9B.
Figure 9D:
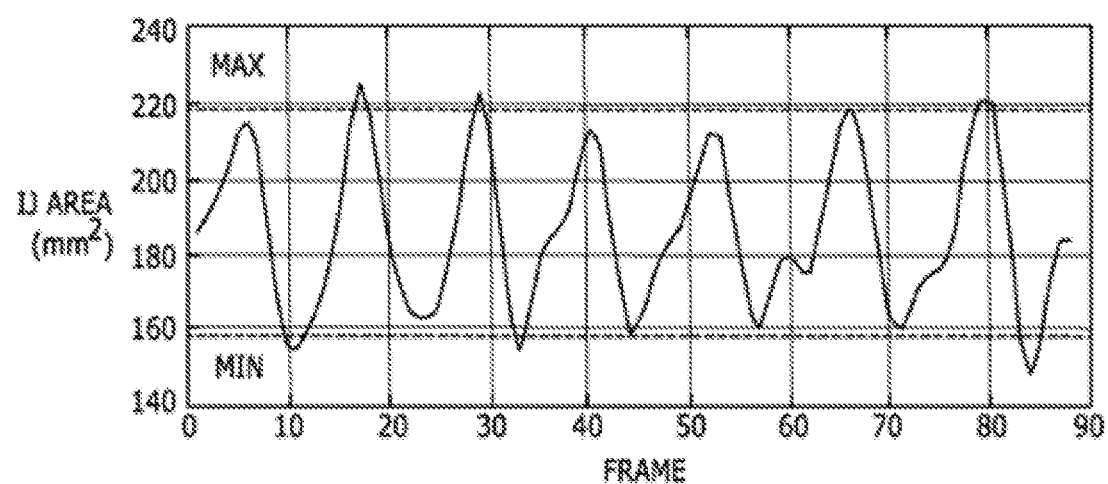
FIG. 9D is a plot of vessel (IJ) area due to cardiac or respiratory variation and illustrating maximum and minimum values for determining a volume responsiveness (VR) index.

Next, at a step 360, the processing system 300 computes the VR index that can be displayed as a time-domain chart. Once a sufficient number of respiration or cardiac cycles worth of data have been collected, geometric parameters can be extracted from the geometric functions for each frame, such as length, circumference, area and ovality. An example of this process is provided in FIGS. 9A & 9B, which illustrate example measurements from the CCA and the IJ using a linear caliper (FIG. 9A) and a spline (FIG. 9B). From these measurements, 2nd order markers such as vessel strain, heart rate, heart rate variability, respiration rate, etc. can be computed. If the flow rate of the blood through the CCA or IJ is known, the cross-sectional vessel area can be used to compute the volume flow through the vessel. If an electrocardiogram (ECG) signal is available, the pulse wave velocity (PWV) can be computed between the ECG and the corresponding increase in carotid strain. PWV has been used to assess cardiovascular risk due to aortic stiffness and even used to estimate blood pressure. FIG. 9C illustrates another example of a spline fitted around a vessel wall using selected tracking markers and vessel area graph over time, similar to that of FIG. 9B. In FIG. 9C, the peeks of the plot are labeled "RED" and corresponding to the corresponding locations in the image, while the troughs are labeled "GREEN". FIG. 9D shows that the vessel area may be plotted over time, by the computer system, as a function of a selected quantity, such as a fluid.

The VR index is obtained by computing the ratio between the difference between the maximum and minimum geometry (preferably IJ cross-sectional area) and the maximum geometry over a series of respiration cycles (see, e.g., FIG. 9D). However, cardiac cycles could also be used. By reviewing the change in ratio over time, the progression of fluid therapy can be determined. As the patient reaches their optimal fluid load, the slope of the ratio will begin to decrease, eventually reaching a plateau when the patient is no longer fluid responsive.

It is understood that the complexity of the collected data would generally not be available to the user in the system 100. Nonetheless, FIGS. 9A and 9B illustrate preliminary data from a healthy subject, showing measurements of temporal changes in any number of vessels, such as the IJ (labeled "BLUE") and the common carotid artery (CCA) (labeled "RED"). In order to obtain a measurement of fluid responsiveness to the administration of IV fluids, the system 100 monitors changes in the volume, area, diameter, and/or shape of the IJ across the respiratory cycle, which provides an indicator of the volume responsiveness of a patient.

In summary, the step 360 includes extracting geometric measurements from the geometric functions for each image frame. These data may require additional filtering. Second order parameters are computed from these data, such as the VR index.

In contrast to existing speckle training applications, the present system utilizes speckle tracking as a tool that forms only a sub-function of the larger system. In the present system, speckle tracked ROIs are used in three distinct ways: 1) to detect (not measure) the location of the source(s) of cyclic tissue motion, 2) to detect (not measure) regions of blood flow by migrating ROI away from these areas, and 3) as empirical data points to calculate the coefficients of a polynomial equation describing the vessel geometry.

Additionally, the present processing system need not use strain or perform any spatial measurements. Rather, the processing system evaluates the PSD associated with the displacement versus time of individual ROI independent of other ROI to identify frequencies embedded in the tissue motion (ROI displacement versus time data). Prior to computing PSD all non-physiologic motion (i.e. motion artifact or freehand compression of the ultrasound sensor against the skin) is removed from the ROI displacement data using filters. Our approach is different from common practice in that when performing conventional ultrasound strain imaging, non-physiologic induced strain (except for cardiac strain measurements) either from freehand compression, acoustic radiation force or other extracorporeal sources are required to obtain the strain data, in conventional techniques.

In conventional techniques, when utilizing typical speckle tracking (decorrelation) to measure blood flow velocity/volume, very high speed A-line/image acquisition rates are utilized (i.e. 300 frames per second or higher). This is to avoid gross changes in speckle due to the blood flow. This method of blood flow measurement relies on measuring reductions in the correlation (intermediate decorrelation) of the ROI tracking markers induced by blood flow. Conversely, the present processing system relies on a much lower frame rate (i.e., 30 frames per second or less) to cause complete decorrelation between frames, which indicates the ROI correlation-based search algorithm was unable to locate a similar speckle signature between subsequent frames. In this situation, the ROI motion will not be contingent on speckle displacement (since there is no "friction" between the ROI and speckle pattern), but rather on a unique feature that induces a small "thrust" to the ROI, which will continue to move it along a trajectory until it encounters a stable speckle signature that it can lock on to.

Each ROI is assigned a unique pseudorandom thrust vector angle to encourage random migration of the ROI that occur in regions of blood flow. As a result, complete decorrelation may be achieved as opposed to intermediate decorrelation. Further, the described ROI are designed to migrate away from regions of blood flow. Intentional or unintentional motion artifacts are therefore able to help to migrate the ROI from the vessel lumen to improve vessel detection. Other methods may require the ROI remain in a fixed position to measure flow at that specific location between sequential image frames. Any motion artifact may result in gross decorrelation of the image and degrade the flow measurement and vessel identification accuracy unless some form of frame stabilization algorithm is employed.

Once the PSD for each ROI is computed, the image can be rasterized with a minimum value assigned to regions devoid of ROI. Since the peaks of the rasterized PSD will fall along tissue surrounding the blood flow, a clear contrast between the maximum to minimum spatial PSD map can be used to obtain a starting point along the vessel edge ("shoreline" detection algorithm). From this "genesis point," a number of different polynomials could be fit to the minimum of the spatial PSD map (blood flow region) for each frame in order to measure changes in vessel geometry over time. Since the paths of the ROI along the vessel edge will already be known, the ROI can be used as empirical source data when fitting the coefficients of the polynomials. Due to the mechanism of the algorithm, only ROI attached to stable speckle will be available to be used and thereby reducing errors. Changes in the polynomial function over subsequent frames can be used to compute the contractility index (also termed VR index herein) of the vessel utilizing its area, diameter, circumference, ovality, etc.

Figure 10:
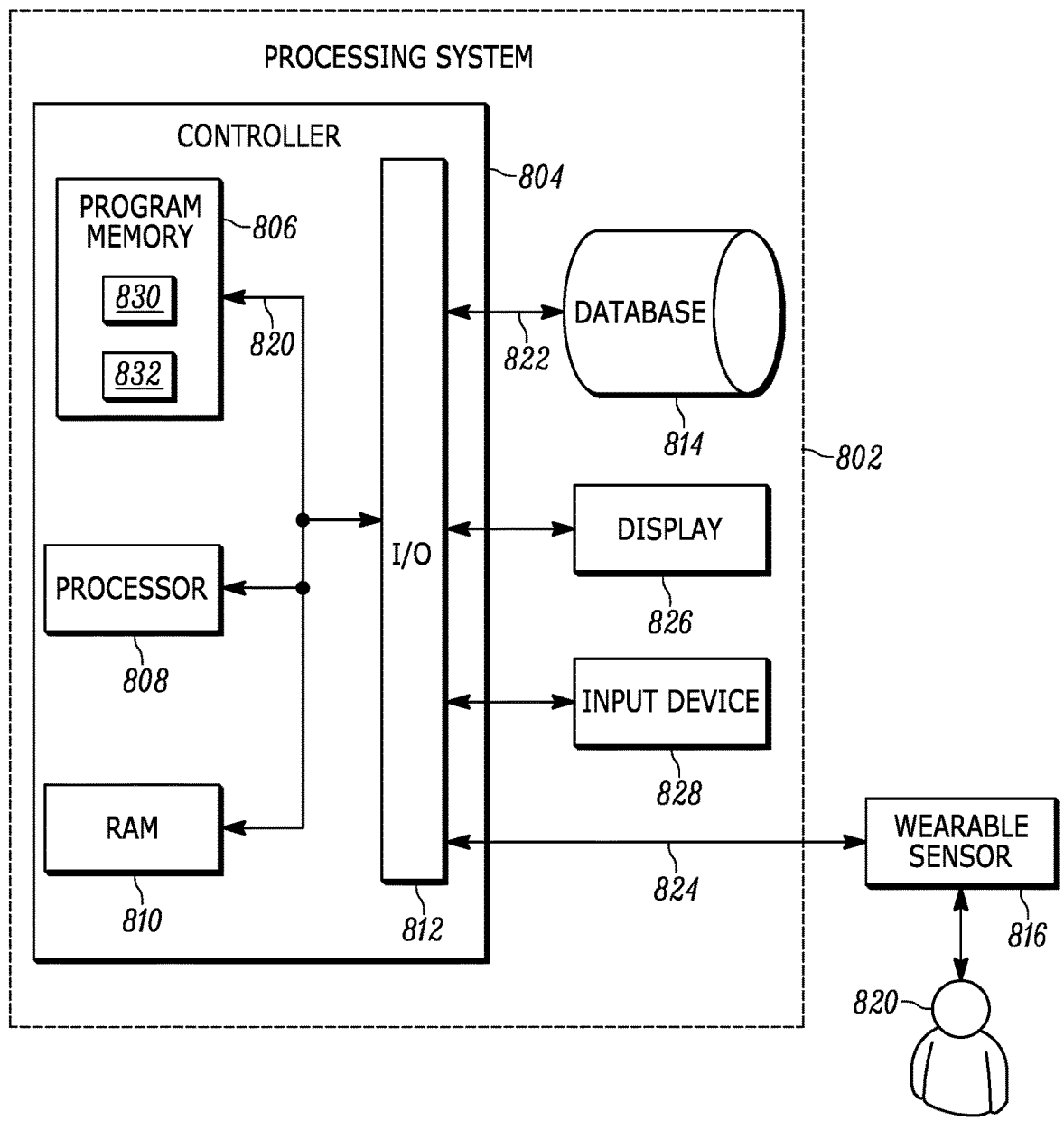
FIG. 10 is a schematic view of a non-invasively, autonomously, and repeatedly measuring and recording changes of vessels over time.

FIG. 10 is an example block diagram 800 illustrating the various components used in implementing an example embodiment of an automated ultrasound apparatus discussed herein. A processing system 802 (or "signal processor") may be coupled to a patient 820 via one or more wearable sensors 816 (or a "wearable sensor assembly") in accordance with executing the functions of the disclosed embodiments. The processing system 802 may have a controller 804 operatively connected to the database 814 via a link 822 connected to an input/output (I/O) circuit 812. It should be noted that, while not shown, additional databases may be linked to the controller 804 in a known manner. The controller 804 includes a program memory 806, one or more processors 808 (may be called microcontrollers or a microprocessors), a random-access memory (RAM) 810, and the input/output (I/O) circuit 812, all of which are interconnected via an address/data bus 820. It should be appreciated that although only one processor 808 is shown, the controller 804 may include multiple microprocessors 808. Similarly, the memory of the controller 804 may include multiple RAMs 810 and multiple program memories 806. Although the I/O circuit 812 is shown as a single block, it should be appreciated that the I/O circuit 812 may include a number of different types of I/O circuits. The RAM(s) 810 and the program memories 806 may be implemented as semiconductor memories, magnetically readable memories, and/or optically readable memories, for example. A link 824, which may include one or more wired and/or wireless (Bluetooth, WLAN, etc.) connections, may operatively connect the controller 804 to a wearable sensor 816 through the I/O circuit 812. The wearable sensor 816 may be operatively connected to the patient 820.

The program memory 806 and/or the RAM 810 may store various applications (i.e., machine readable instructions) for execution by the processor 808. For example, an operating system 830 may generally control the operation of the processing system 802 and provide a user interface to the processing system 802 to implement the process described herein. The program memory 806 and/or the RAM 810 may also store a variety of subroutines 832 for accessing specific functions of the processing system 802. By way of example, and without limitation, the subroutines 832 may include, among other things: a subroutine for taking measurements with the wearable sensor 816, a subroutine for filtering measurement (or data) from the wearable sensor 816, a subroutine for performing signal decomposition on raw signal data from the wearable sensor 816, and a subroutine for extracting one or more features of a sensing region from the raw signal data from the wearable sensor 816. The subroutines 832 may also include other subroutines, for example, implementing software keyboard functionality, interfacing with other hardware in the processing system 802, etc. The program memory 806 and/or the RAM 810 may further store data related to the configuration and/or operation of the processing system 802, and/or related to the operation of the one or more subroutines 832. For example, the data may be data gathered by the wearable sensor 816, data determined and/or calculated by the processor 808, etc. In addition to the controller 804, the processing system 802 may include other hardware resources. The processing system 802 may also include various types of input/output hardware such as a visual display 826 and input device(s) 828 (e.g., keypad, keyboard, etc.). In an embodiment, the display 826 is touch-sensitive, and may cooperate with a software keyboard routine as one of the software routines 832 to accept user input. It may be advantageous for the processing system 802 to communicate with a broader medical treatment network (not shown) through any of a number of known networking devices and techniques (e.g., through a commuter network such as a hospital or clinic intranet, the Internet, etc.). For example, the testing apparatus may be connected to a medical records database, hospital management processing system, health care professional terminals (e.g., doctor stations, nurse stations), patient monitoring systems, automated drug delivery systems such as smart pumps, smart infusion systems, automated drug delivery systems, etc. Accordingly, the disclosed embodiments may be used as part of an automated closed loop system or as part of a decision assist system.

Although depicted as separate entities or components in FIG. 10, it is understood that any or the entire signal processing functionality and/or components of the processing system 802 may be combined with a wearable sensor assembly, such as the wearable sensor 816. In this manner, a wearable sensor may both gather data about the patient 820 and process the gathered data to extract one or more waveform features, as discussed further below. Also, although depicted as a single component in FIG. 10, the wearable sensor 816 may include multiple of the same type or different types of sensors. For example, the wearable sensor 816 may include both a piezoelectric sensor for measuring raw signal data and a secondary sensor for collecting photoplethysmograph derived blood flow and hemoglobin oxygen saturation data. In some examples, the wearable sensor 816 may be implemented with one or more of a variety of other (or secondary) sensors, such as temperature sensors, motion sensors, actigraphy sensors, galvanic skin response sensors, impedance sensors, etc.

The systems described herein provide an ultra-low cost device that may potentially be disposable, thus alleviating concerns related to hospital equipment management (tracking, cleaning and delivery) associated with ultrasound hardware. Further, the system is ultra-lightweight and low profile, which minimizes motion artifacts and patient discomfort. An operator does not need to physically hold the probe to collect data. Accordingly, automated data collection is feasible. Further, the system provides the ability to customize imaging widths (e.g., scan lengths) for various applications and is not limited by the associated imaging hardware. Curvature or flexibility can be incorporated into the design for improved fit to the anatomy of the patient.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, nonvolatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

What is claimed:

1. A system comprising:
   a patch-type imaging ultrasound sensor configured to attach to a patient;
   an ultrasound scanning system including a single-element transducer configured to acquire low-level ultrasound data from the sensor such that at least one of 2 dimensional planes or 3-dimensional volumes are automatically acquired; and
   a processing system configured to perform a data acquisition sequence in which the low-level ultrasound data is collected and to perform signal and image processing of the low-level ultrasound data to automatically convert the low level ultrasound data into a numerical measurement;
   wherein the sensor is communicatively coupled to the ultrasound scanning system and the processing system, the processing system configured to utilize a swarm speckle tracking approach to:
   automatically measure tissue motion of a tissue to determine a presence or absence and respective location of at least one vein,
   discriminate between other vessels and identify a presence or absence of a specific vein within a pre-specified anatomic region,
   identify a vessel wall region of the specific vein,
   automatically select a plurality of tracking markers residing at locations near the vessel wall region,
   automatically assign a unique pseudorandom thrust vector to each of the plurality of tracking markers,
   automatically track and analyze a movement of the tracking markers over at least one respiratory and cardiac cycle, wherein the movement is representative of temporal geometric changes, and
   compute a contractility index based on the temporal geometric changes of the vessel wall region, wherein the contractility index is computed by computing a ratio between:
      (i) a difference between a maximum geometry and a minimum geometry of the vessel wall region, and
      (ii) the maximum geometry, over the at least one respiratory and cardiac cycle according to the movement of the tracking markers such that at least one measurement of the specific vein can be computed for each 2-dimensional plane or 3-dimensional volume obtained.

2. The system of claim 1, wherein the at least one measurement of the specific vein comprises a circumference and a cross-sectional area of the specific vein, and further comprises at least one of a diameter, major axis, or minor axis of the specific vein.

3. The system of claim 1, wherein the processing system is configured to automatically remove motion artifacts and unwanted pulsations from the tissue motion.

4. The system of claim 3, wherein the processing system is configured to calculate at least one ratio between any two of: maximum, mean, median, mode, and minimum measurements, wherein the measurements are measurements of a cross-section of the specific vein and the measurements of the cross-section of the specific vein vary as a function of respiration or heartbeat.

5. The system of claim 1, wherein the processing system is configured to determine a position, orientation, and geometry parameter of a shape approximately oval or circular approximating the specific vein, by utilizing a cost function based on an image intensity and a tissue motion map obtained from computing a point spread distribution of the tracking markers.

6. The system of claim 1, wherein the processing system is configured to output at least one measurement to an output display communicatively coupled to the processing system to provide an instantaneous indication or trend reflecting temporal changes in vessel geometry based at least in part on at least one measurement obtained from the specific vein.

7. The system of claim 1, wherein the specific vein comprises an internal jugular vein (IJ).

8. The system of claim 1, wherein the specific vein comprises a femoral vein.

9. The system of claim 1, wherein the processing system is configured to detect a single measurement across a plurality of respiratory or cardiac cycles, wherein the single measurement is one of: a mean diameter, a median diameter, a mode diameter, a maximum diameter, and a minimum diameter of the specific vein across a plurality of respiratory or cardiac cycles.

10. The system of claim 1, wherein the processing system is configured to detect the specific vein by tracking motion of a plurality of regions dispersed across an image generated by the sensor with sufficient granularity to allow a resulting motion vector field to determine a region from which the motion originated, wherein a frequency domain transformation is applied to a motion path comprising each point in the motion vector field versus time or over a specified time segment in order to identify regions within the image that exhibit periodic tissue motion, and wherein the processing system is configured to compute (i) spatial statistical metrics for motion paths for each point in the motion vector field, and (ii) associated correlation data over time or a specified time segment in order to identify regions within the image that exhibit temporal instability due to tissue motion.

11. The system of claim 1, wherein the processing system is configured to initially capture a reference cine loop and to compare to subsequent cine loops and to determine changes in an image generated by the sensor due to a change in vessel geometry.

12. The system of claim 1, wherein the ultrasound scanning system is configured to transmit a plurality of 2-dimensional ultrasound planes to form a 3-dimensional data set from which vessel wall regions of the at least one vein are detected so as to determine a size and a volume of a first vein of the at least one vein and a second vein of the at least one vein in real time.

13. The system of claim 1, wherein the ultrasound scanning system is configured to steer a single ultrasound beam such that it intersects a targeted point in the tissue, to hold the targeted point, and to acquire ultrasound data along a single beam over time in order to obtain M-mode data showing geometry changes over time, or to compute the correlation between successive beams in order to measure blood flow speed over time, wherein once the blood flow speed and a vein cross-sectional area are known, a volume flow through the vein can be computed.

14. The system of claim 1, wherein the ultrasound scanning system is configured to steer a 2-dimensional ultrasound scan plane such that it coincides with a target plane in the tissue, hold the targeted plane, and acquire ultrasound data from the target plane over time.

15. The system of claim 1, wherein the processing system is configured to continuously measure at least one of a respiration rate, a heart rate, or a heart rate variability by monitoring changes in vessel geometry over time for the specific vein.

16. The system of claim 1, wherein the processing system is configured to noninvasively measure a variation in at least one diameter, major axis, minor axis, area, or circumference of the specific vein instantaneously and over time.

17. The system of claim 1, wherein the specific vein is a plurality of veins including a first vein and a second vein, and wherein the processing system is configured to assess a roundness of the first vein and the second vein by comparing a plurality of diameters, major axes, minor axes, or other geometric measurements to respiration or heart rate to differentiate a collapse of the first vein and the second vein from a reduced diameter, major axis, or minor axis of the first vein and the second vein.

18. The system of claim 17, wherein the processing system is configured to compute a collapsibility of the specific vein by at least one of: (i) using an integral or derivative of a ratio between a maximum to minimum diameter, major axis, or minor axis versus respiration or heart rate, or (ii) determining an origin of a vessel pulsation and calculating an integral or derivative or the ratio between a maximum to minimum radius from the origin versus respiration or heart rate.

19. The system of claim 1, wherein the sensor comprises a flat or concave surface that enables the sensor to lay flush to a skin surface.

20. The system of claim 1, wherein the sensor comprises a self-adhering structure to facilitate fixation and positioning of the sensor on one of a neck and a thigh of the patient, wherein the self-adhering structure includes a disposable adhesive pad and wherein a gel pocket is provided to facilitate acoustic coupling between the sensor and the patient.

21. The system of claim 1, wherein the processing system is configured to compare geometric measurements between at least two vessels and to calculate a ratio.

22. The system of claim 1, wherein the ultrasound scanning system is configured to acquire Doppler or speckle decorrelation flow data to compute blood flow velocity data.

23. The system of claim 22, wherein the processing system is configured to combine the blood flow velocity data and geometric data obtained from the ultrasound scanning system to compute a volume of blood flowing through the at least one vein.

24. The system of claim 23, wherein the processing system is configured to compute variations in blood volume flow as a function of time due to respiration and heart rate.

25. The system of claim 1, wherein at least a portion of the sensor is rotatable, the system further comprising a drive system to drivingly rotate the sensor about a rotational axis.

26. The system of claim 1, wherein the processing system utilizes a phase shift of vessel wall motion due to cardiac and/or respiratory artifacts to discriminate veins from arteries.

27. The system of claim 1, wherein the processing system is configured to compute a power spectral density of a frequency spectrum of tracking marker paths resulting from the tissue motion to identify regions of periodic tissue pulsation originating from vessels.

* * * * *

UNITED STATES PATENT AND TRADEMARK OFFICE
CERTIFICATE OF CORRECTION

PATENT NO. : 11,701,092 B2  
APPLICATION NO. : 16/611470  
DATED : July 18, 2023  
INVENTOR(S) : Grant Kruger et al.

Page 1 of 1

It is certified that error appears in the above-identified patent and that said Letters Patent is hereby corrected as shown below:

On the Title Page

Item (73), Line 1, "REGENTS" should be -- THE REGENTS --.

Signed and Sealed this
Twenty-ninth Day of July, 2025

Coke Morgan Stewart
*Acting Director of the United States Patent and Trademark Office*